(12) United States Patent
Neumann

(10) Patent No.: US 11,154,240 B2
(45) Date of Patent: Oct. 26, 2021

(54) METHODS AND SYSTEMS FOR UTILIZING DIAGNOSTICS FOR INFORMED VIBRANT CONSTITUTIONAL GUIDANCE

(71) Applicant: Kenneth Neumann, Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 0 days.

(21) Appl. No.: 16/372,512

(22) Filed: Apr. 2, 2019

(65) Prior Publication Data

US 2020/0315527 A1    Oct. 8, 2020

(51) Int. Cl.
*G16H 10/40* (2018.01)
*A61B 5/00* (2006.01)
(Continued)

(52) U.S. Cl.
CPC .......... *A61B 5/4842* (2013.01); *A61B 5/7267* (2013.01); *A61B 5/7275* (2013.01);
(Continued)

(58) Field of Classification Search
CPC . A61B 5/4842; A61B 5/04012; A61B 5/0482; A61B 5/04845; A61B 5/165; A61B 5/441; A61B 5/486; A61B 5/742
(Continued)

(56) References Cited

U.S. PATENT DOCUMENTS

| 8,271,415 B2 | 9/2012 | Iliff |
| 8,370,070 B2 | 2/2013 | Fernandez |

(Continued)

FOREIGN PATENT DOCUMENTS

| WO | 2008058399 | 5/2008 |
| WO | 1904006347 | 1/2014 |

(Continued)

OTHER PUBLICATIONS

Ruihua Guo et al., Tuberculosis diagnostics and localization in Chest Rays via Deep learning model, Front. Artf. Intell, 2020; https://www.frontiersin.org/journals/10.3389/frai.2020.583427/full (Year: 2020).*

(Continued)

*Primary Examiner* — Hiep V Nguyen
(74) *Attorney, Agent, or Firm* — Caldwell Intellectual Property Law, LLC

(57) ABSTRACT

A system for utilizing diagnostics for informed vibrant constitutional guidance includes a diagnostic engine operating on at least a server and configured to receive a first training set including a plurality of first data entries, receive a second training set including a plurality of second data entries, receive at least a biological extraction from a user and generate a diagnostic output including at least a prognostic label and at least an ameliorative process label using the first training set, the second training set, and the at least a biological extraction. The system includes at least an advisory module operating on at least the server and configured to generate at least an advisory output as a function of the diagnostic output and transmit the at last an advisory output to at least an advisor client device.

20 Claims, 20 Drawing Sheets

(51) Int. Cl.
G06N 20/00 (2019.01)
G16H 50/20 (2018.01)

(52) U.S. Cl.
CPC ............ G06N 20/00 (2019.01); G16H 10/40 (2018.01); G16H 50/20 (2018.01)

(58) Field of Classification Search
USPC .......................................................... 705/2
See application file for complete search history.

(56) References Cited

U.S. PATENT DOCUMENTS

| | | | |
|---|---|---|---|
| 8,532,938 B2 | 9/2013 | Jung et al. | |
| 8,697,370 B2 | 4/2014 | Kas et al. | |
| 8,762,167 B2 | 6/2014 | Blander et al. | |
| 9,120,852 B2 | 9/2015 | Jouhanneaud | |
| 9,207,242 B2 | 12/2015 | Luk et al. | |
| 2004/0122787 A1 | 6/2004 | Avinash et al. | |
| 2010/0267052 A1 | 10/2010 | Gelber et al. | |
| 2011/0230733 A1 | 9/2011 | Al-Ali | |
| 2014/0296327 A1* | 10/2014 | Bueno ................. | A61K 31/566 514/44 R |
| 2014/0310019 A1 | 10/2014 | Blander et al. | |
| 2015/0079033 A1 | 3/2015 | Shuber et al. | |
| 2015/0252436 A1 | 9/2015 | Samant et al. | |
| 2016/0068916 A1 | 3/2016 | Nekarda et al. | |
| 2016/0367188 A1 | 12/2016 | Malik et al. | |
| 2018/0032698 A1 | 2/2018 | Lau et al. | |
| 2018/0106807 A1 | 4/2018 | Redston | |
| 2018/0306804 A1 | 10/2018 | Micallef et al. | |
| 2019/0025333 A1 | 1/2019 | Zhang et al. | |
| 2019/0074080 A1 | 3/2019 | Appelbaum et al. | |
| 2019/0078142 A1 | 3/2019 | Apte et al. | |
| 2019/0087536 A1 | 3/2019 | Apte et al. | |

FOREIGN PATENT DOCUMENTS

| | | | |
|---|---|---|---|
| WO | 2014071455 | 5/2014 | |
| WO | 2015085368 | 6/2015 | |
| WO | WO-2015085368 A1 * | 6/2015 | ......... G01N 33/6869 |
| WO | 2017044885 | 3/2017 | |
| WO | 2017044902 | 3/2017 | |
| WO | 2018020239 | 2/2018 | |

OTHER PUBLICATIONS

MagMAX Core Nucleic Acid Purification Kit, Flyer, 2019, ThermoFisher Scientific.

* cited by examiner

METHODS AND SYSTEMS FOR UTILIZING DIAGNOSTICS FOR INFORMED VIBRANT CONSTITUTIONAL GUIDANCE

FIELD OF THE INVENTION

The present invention generally relates to the field of diagnostics. In particular, the present invention is directed to methods and systems for utilizing diagnostics for informed vibrant constitutional guidance.

BACKGROUND

Automated analysis of data and correct transmission of said data can be challenging due to the complexity of and multiplicity of data to be analyzed. Knowing which data should be transmitted to which skilled professional can be highly complex due to the unique and individual needs of each user—a problem exacerbated by the burgeoning volume of data available for analysis. Transmissions to incorrect professionals can lead to inaccuracies within systems, waste time trying to correct cumbersome issues, and ultimately frustrate users.

SUMMARY OF THE DISCLOSURE

Aspects of the present disclosure are directed to a system for utilizing diagnostics for informed vibrant constitutional guidance. The system includes a diagnostic engine operating on a server. The diagnostic engine is configured to receive a first training set including a plurality of first data entries, each first data entry of the plurality of first data entries including at least an element of physiological state data and at least a correlated first prognostic label. The diagnostic engine receives a second training set including a plurality of second data entries, each second data entry of the plurality of second data entries including at least a second prognostic label and at least a correlated ameliorative process label. The diagnostic engine receives at least a biological extraction from a user. The diagnostic engine generates a diagnostic output based on the at least a biological extraction. The diagnostic output includes at least a prognostic label and at least an ameliorative process label using the first training set, the second training set, and the at least a biological extraction. The system includes at least an advisory module operating on the server. The advisory module is configured to generate at least an advisory output as a function of the diagnostic output. The advisory module transmits the at least an advisory output to at least an advisor client device.

Aspects of the present disclosure are directed to a method of utilizing diagnostics for informed vibrant constitutional guidance. The method includes receiving by a diagnostic engine operating on a server training data. The method includes receiving by the diagnostic engine operating on the server at least a biological extraction from a user. The method includes generating by the diagnostic engine operating on the server a diagnostic output including at least a prognostic label and at least an ameliorative process label. The method includes transmitting by the diagnostic engine operating on the server the diagnostic output to at least an advisor client device. The method includes generating by at least an advisory module operating on the server at least an advisory output as a function of the diagnostic output. The method includes transmitting by the at least an advisory module operating on the server the at least an advisory output to at least an advisor client device.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for utilizing diagnostics for informed vibrant constitutional guidance. In an embodiment, classification of biological extractions to one or more prognostic labels is accomplished using training set data. Prognostic labels are further linked to ameliorative process labels using additional training sets. Prognostic and ameliorative labels are utilized to generate a diagnostic output. Diagnostic output is then utilized to generate at least an advisory output. Advisory output may then be transmitted to an advisor client device which may be operated by an informed advisor which may include a network of functional medicine professionals, spiritual professionals, nutrition professionals, fitness professionals, family and friends, electronic behavior coaches, artificial intelligence advisors, and miscellaneous advisors.

Figure 1:
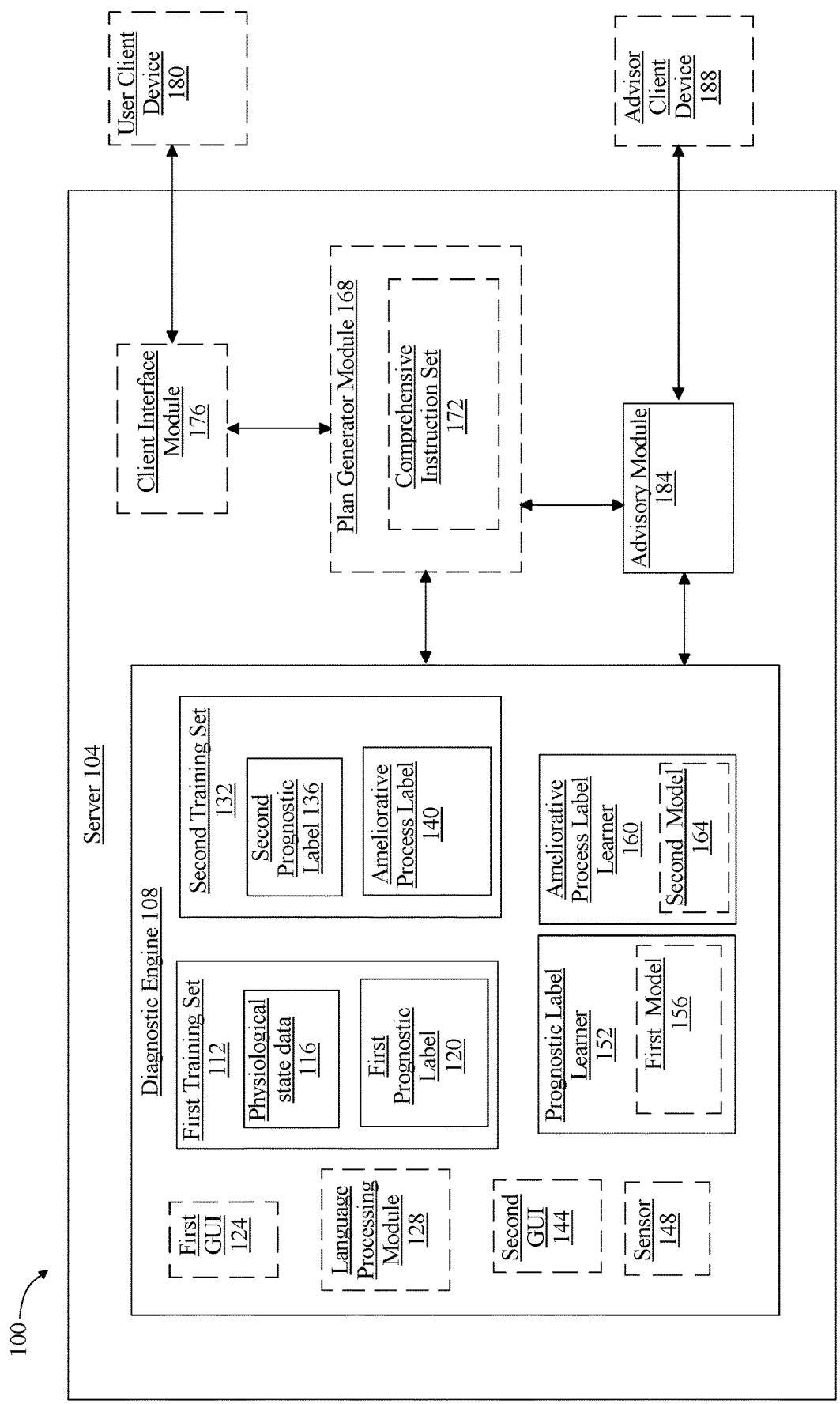
FIG. 1 is a block diagram illustrating an exemplary embodiment of a system for utilizing diagnostics for informed vibrant constitutional guidance.

Turning now to FIG. 1, a system 100 for utilizing diagnostics for informed vibrant constitutional guidance is illustrated. Turning now to FIG. 1, an artificial intelligence advisory system 100 for vibrant constitutional guidance. Artificial intelligence advisory system includes at least a server 104. At least a server 104 may include any computing device as described below in reference to FIG. 19, including without limitation a microcontroller, microprocessor, digital signal processor (DSP) and/or system on a chip (SoC) as described below in reference to FIG. 19. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

Still referring to FIG. 1, system 100 includes a diagnostic engine 108 operating on the at least a server 104, wherein the diagnostic engine 108 configured to receive a first training set including a plurality of first data entries, each first data entry of the plurality of first data entries including at least an element of physiological state data and at least a correlated first prognostic label; receive a second training set including a plurality of second data entries, each second data entry of the plurality of second data entries including at least a second prognostic label and at least a correlated ameliorative process label; receive at least a biological extraction from a user; and generate a diagnostic output based on the at least a biological extraction, the diagnostic output including at least a prognostic label and at least an ameliorative process label using the first training set, the second training set, and the at least a biological extraction. At least a server 104, diagnostic engine 108, and/or one or more modules operating thereon may be designed and/or configured to perform any method, method step, or sequence of method steps in any embodiment described in this disclosure, in any order and with any degree of repetition. For instance, at least a server 104 and/or diagnostic engine 108 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 and/or diagnostic engine 108 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 1, diagnostic engine 108 may be designed and configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, diagnostic engine 108 may be configured to receive a first training set 112 including a plurality of first data entries, each first data entry of the first training set 112 including at least an element of physiological state data 116 and at least a correlated first prognostic label 120. At least an element of physiological state data 116 may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data 116 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data 116 may include, without limitation, immune function data such as Interleukine-6 (IL-6), TNF-alpha, systemic inflammatory cytokines, and the like.

Continuing to refer to FIG. 1, physiological state data 116 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data 116 may include measures of glucose metabolism such as fasting glucose levels and/or hemoglobin A1-C(HbA1c) levels. Physiological state data 116 may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data 116 may include measures of estimated glomerular filtration rate (eGFR). Physiological state data 116 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data 116 may include antinuclear antibody levels. Physiological state data 116 may include aluminum levels. Physiological state data 116 may include arsenic levels. Physiological state data 116 may include levels of fibrinogen, plasma cystatin C, and/or brain natriuretic peptide.

Continuing to refer to FIG. 1, physiological state data 116 may include measures of lung function such as forced expiratory volume, one second (FEV-1) which measures how much air can be exhaled in one second following a deep inhalation, forced vital capacity (FVC), which measures the volume of air that may be contained in the lungs. Physiological state data 116 may include a measurement blood pressure, including without limitation systolic and diastolic blood pressure. Physiological state data 116 may include a measure of waist circumference. Physiological state data 116 may include body mass index (BMI). Physiological state data 116 may include one or more measures of bone mass and/or density such as dual-energy x-ray absorptiometry. Physiological state data 116 may include one or more measures of muscle mass. Physiological state data 116 may include one or more measures of physical capability such as without limitation measures of grip strength, evaluations of standing balance, evaluations of gait speed, pegboard tests, timed up and go tests, and/or chair rising tests.

Still viewing FIG. 1, physiological state data 116 may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data 204 may include one or more measures of psychological function or state, such as without limitation clinical interviews, assessments of intellectual functioning and/or intelligence quotient (IQ) tests, personality assessments, and/or behavioral assessments. Physiological state data 204 may include one or more psychological self-assessments, which may include any self-administered and/or automatedly computer-administered assessments, whether administered within system 100 and/or via a third-party service or platform.

With continued reference to FIG. 1, physiological state data 116 may include one or more evaluations of sensory ability, including measures of audition, vision, olfaction, gustation, vestibular function and pain. Physiological state data 116 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data 116 may include proteomic data, which as used herein, is data describing all proteins produced and/or modified by an organism, colony of organisms, or system of organisms, and/or a subset thereof. Physiological state data 116 may include data concerning a microbiome of a person, which as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data 116 of a person, and/or on prognostic labels and/or ameliorative processes as described in further detail below. Physiological state data 116 may include any physiological state data 116, as described above, describing any multicellular organism living in or on a person including any parasitic and/or symbiotic organisms living in or on the persons; non-limiting examples may include mites, nematodes, flatworms, or the like. Examples of physiological state data 116 described in this disclosure are presented for illustrative purposes only and are not meant to be exhaustive. Persons skilled in the art, upon reviewing the entirety of this disclosure, will be aware of various additional examples of physiological state data 116 that may be used consistently with descriptions of systems and methods as provided in this disclosure.

Continuing to refer to FIG. 1, each element of first training set 112 includes at least a first prognostic label 120. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or heathy aging. At least a prognostic label may be associated with a physical and/or somatic condition, a mental condition such as a mental illness, neurosis, or the like, or any other condition affecting human health that may be associated with one or more elements of physiological state data 116 as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrinal disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 1, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

With continued reference to FIG. 1, in each first data element of first training set 112, at least a first prognostic label 120 of the data element is correlated with at least an element of physiological state data 116 of the data element. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the first training set 112. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 112 and/or first data element consistently with this disclosure.

In an embodiment, and still referring to FIG. 1, diagnostic engine 108 may be designed and configured to associate at least an element of physiological state data 116 with at least a category from a list of significant categories of physiological state data 116. Significant categories of physiological state data 116 may include labels and/or descriptors describing types of physiological state data 116 that are identified as being of high relevance in identifying prognostic labels. As a non-limiting example, one or more categories may identify significant categories of physiological state data 116 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 1, diagnostic engine 108 may receive the list of significant categories according to any suitable process; for instance, and without limitation, diagnostic engine 108 may receive the list of significant categories from at least an expert. In an embodiment, diagnostic engine 108 and/or a user device connected to diagnostic engine 108 may provide a graphical user interface, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like Still referring to FIG. 1, diagnostic engine 108 may receive the list of significant categories according to any suitable process; for instance, and without limitation, diagnostic engine 108 may receive the list of significant categories from at least an expert. In an embodiment, diagnostic engine 108 and/or a user device connected to diagnostic engine 108 may provide a graphical user interface 124, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface 124 or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface 124 may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like Referring again to FIG. 1, data information describing significant categories of physiological data, relationships of such categories to prognostic labels, and/or significant categories of prognostic labels may alternatively or additionally be extracted from one or more documents using a language processing module 128. Language processing module 128 may include any hardware and/or software module. Language processing module 128 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 128 may compare extracted words to categories of physiological data recorded at diagnostic engine 108, one or more prognostic labels recorded at diagnostic engine 108, and/or one or more categories of prognostic labels recorded at diagnostic engine 108; such data for comparison may be entered on diagnostic engine 108 as described above using expert data inputs or the like. In an embodiment, one or more categories may be enumerated, to find total count of mentions in such documents. Alternatively or additionally, language processing module 128 may operate to produce a language processing model. Language processing model may include a program automatically generated by diagnostic engine 108 and/or language processing module 128 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at diagnostic engine 108, or the like.

Still referring to FIG. 1, language processing module 128 and/or diagnostic engine 108 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 128 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 128 may use a corpus of documents to generate associations between language elements in a language processing module 128, and diagnostic engine 108 may then use such associations to analyze words extracted from one or more documents and determine that the one or more documents indicate significance of a category of physiological data, a given relationship of such categories to prognostic labels, and/or a given category of prognostic labels. In an embodiment, diagnostic engine 108 may perform this analysis using a selected set of significant documents, such as documents identified by one or more experts as representing good science, good clinical analysis, or the like; experts may identify or enter such documents via graphical user interface as described above in reference to FIG. 9, or may communicate identities of significant documents according to any other suitable method of electronic communication, or by providing such identity to other persons who may enter such identifications into diagnostic engine 108. Documents may be entered into diagnostic engine 108 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine 108 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to prognostic labels, and/or a given category of prognostic labels is entered via graphical user interface, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of physiological sample, which then may be subjected to ranking, comparison to thresholds and/or elimination as described above.

Still referring to FIG. 1, diagnostic engine 108 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, diagnostic engine 108 may be configured, for instance as part of receiving the first training set 112, to associate at least correlated first prognostic label 120 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result diagnostic engine 108 may modify list of significant categories to reflect this difference.

Still referring to FIG. 1, diagnostic engine 108 is designed and configured to receive a second training set 132 including a plurality of second data entries. Each second data entry of the second training set 132 includes at least a second prognostic label 136; at least a second prognostic label 136 may include any label suitable for use as at least a first prognostic label 120 as described above. Each second data entry of the second training set 132 includes at least an ameliorative process label 140 correlated with the at least a second prognostic label 136, where correlation may include any correlation suitable for correlation of at least a first prognostic label 120 to at least an element of physiological data as described above. As used herein, an ameliorative process label 140 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more medications. Persons skilled in the art, upon reviewing the entirety of this disclosure, will be aware of various processes that may be used as ameliorative processes consistently with this disclosure.

Continuing to refer to FIG. 1, in an embodiment diagnostic engine 108 may be configured, for instance as part of receiving second training set 132, to associate the at least second prognostic label 136 with at least a category from a list of significant categories of prognostic labels. This may be performed as described above for use of lists of significant categories with regard to at least a first prognostic label 120. Significance may be determined, and/or association with at least a category, may be performed for prognostic labels in first training set 112 according to a first process as described above and for prognostic labels in second training set 132 according to a second process as described above.

Still referring to FIG. 1, diagnostic engine 108 may be configured, for instance as part of receiving second training set 132, to associate at least a correlated ameliorative process label 140 with at least a category from a list of significant categories of ameliorative process labels 136. In an embodiment, diagnostic engine 108 and/or a user device connected to diagnostic engine 108 may provide a second graphical user interface 144 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 128 or the like as described above.

In an embodiment, and still referring to FIG. 1, diagnostic engine 108 may extract at least a second data entry from one or more documents; extraction may be performed using any language processing method as described above. Diagnostic engine 108 may be configured, for instance as part of receiving second training set 132, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an ameliorative process label 140; for instance, the medical history document may list a therapy, recommendation, or other ameliorative process that a medical practitioner described or recommended to a patient. A medical history document may describe an outcome; for instance, medical history document may describe an improvement in a condition describing or described by a prognostic label, and/or may describe that the condition did not improve. Prognostic labels, ameliorative process labels 136, and/or efficacy of ameliorative process labels 136 may be extracted from and/or determined from one or more medical history documents using any processes for language processing as described above; for instance, language processing module 128 may perform such processes. As a non-limiting example, positive and/or negative indications regarding ameliorative processes identified in medical history documents may be determined in a manner described above for determination of positive and/or negative indications regarding categories of physiological data, relationships of such categories to prognostic labels, and/or categories of prognostic labels.

Figure 2:
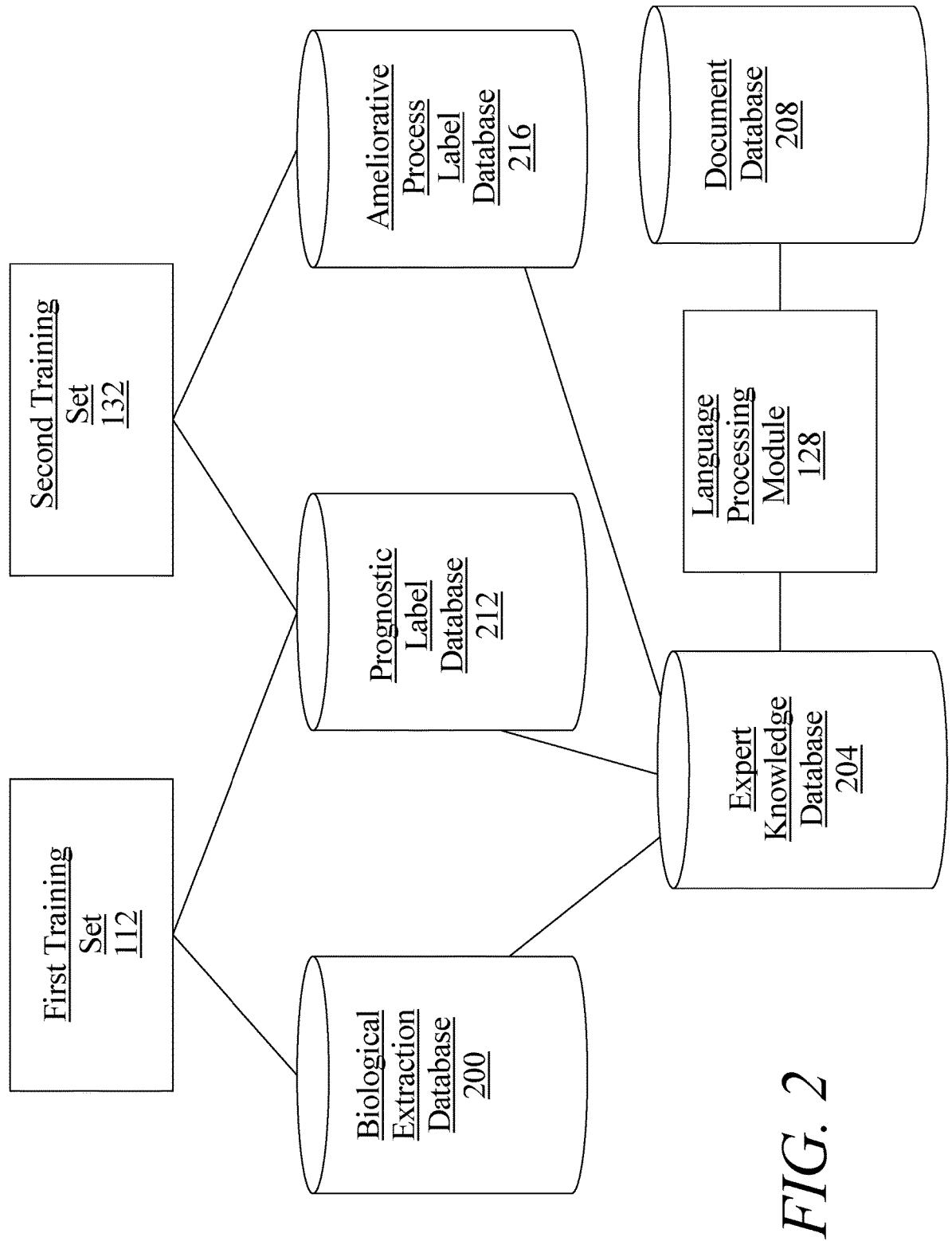
FIG. 2 is a block diagram illustrating embodiments of data storage facilities for use in disclosed systems and methods.

With continued reference to FIG. 2, diagnostic engine 108 may be configured to have a feedback mechanism. In an embodiment, diagnostic engine 108 may be configured to receive a first training set 200 and/or a second training set 220 generated by system 100. For example, data about a user that has been previously been analyzed by diagnostic engine 108 may be utilized in algorithms by first model 240 and/or second model 248. Such algorithms may be continuously updated as a function of such data. In yet another embodiment, data analyzed by language processing module 216 may be utilized as part of training data generating algorithms by first model 240 and/or second model 248 and/or any other machine learning process performed by diagnostic engine 108.

With continued reference to FIG. 1, diagnostic engine 108 may be configured, for instance as part of receiving second training set 132, to receiving at least a second data entry of the plurality of second data entries from at least an expert. This may be performed, without limitation using second graphical user interface as described above.

Referring now to FIG. 2, data incorporated in first training set 112 and/or second training set 132 may be incorporated in one or more databases. As a non-limiting example, one or elements of physiological state data may be stored in and/or retrieved from a biological extraction database 200. A biological extraction database 200 may include any data structure for ordered storage and retrieval of data, which may be implemented as a hardware or software module. A biological extraction database 200 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 200 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related prognostic labels. Data entries may include prognostic labels and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a biological extraction database 200 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of physiological data as described above. Additional elements of information may include descriptions of particular methods used to obtain physiological samples, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a biological extraction database 200 may reflect categories, cohorts, and/or populations of data consistently with this disclosure.

Figure 3:
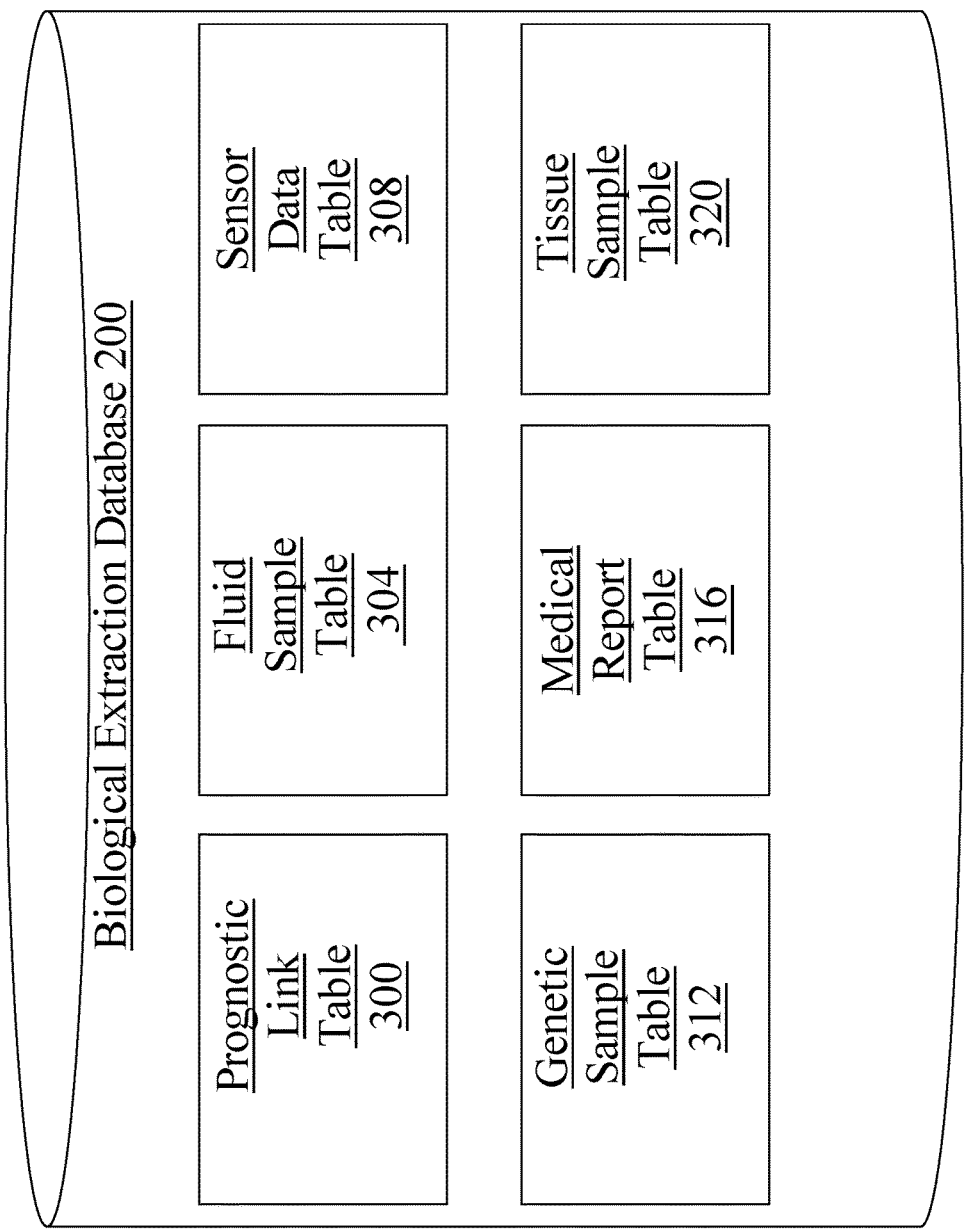
FIG. 3 is a block diagram illustrating an exemplary embodiment of a biological extraction database.

Referring now to FIG. 3, one or more database tables in biological extraction database 200 may include, as a non-limiting example, a prognostic link table 300. Prognostic link table 300 may be a table relating physiological sample data as described above to prognostic labels; for instance, where an expert has entered data relating a prognostic label to a category of physiological sample data and/or to an element of physiological sample data via first graphical user interface 124 as described above, one or more rows recording such an entry may be inserted in prognostic link table 300. Alternatively or additionally, linking of prognostic labels to physiological sample data may be performed entirely in a prognostic label database as described below.

With continued reference to FIG. 3, biological extraction database 200 may include tables listing one or more samples according to sample source. For instance, and without limitation, biological extraction database 200 may include a fluid sample table 304 listing samples acquired from a person by extraction of fluids, such as without limitation blood, lymph cerebrospinal fluid, or the like. As another non-limiting example, biological extraction database 200 may include a sensor data table 308, which may list samples acquired using one or more sensors, for instance as described in further detail below. As a further non-limiting example, biological extraction database 200 may include a genetic sample table 312, which may list partial or entire sequences of genetic material. Genetic material may be extracted and amplified, as a non-limiting example, using polymerase chain reactions (PCR) or the like. As a further example, also non-limiting, biological extraction database 200 may include a medical report table 316, which may list textual descriptions of medical tests, including without limitation radiological tests or tests of strength and/or dexterity or the like. Data in medical report table may be sorted and/or categorized using a language processing module 312, for instance, translating a textual description into a numerical value and a label corresponding to a category of physiological data; this may be performed using any language processing algorithm or algorithms as referred to in this disclosure. As another non-limiting example, biological extraction database 200 may include a tissue sample table 320, which may record physiological samples obtained using tissue samples. Tables presented above are presented for exemplary purposes only; persons skilled in the art will be aware of various ways in which data may be organized in biological extraction database 200 consistently with this disclosure.

Referring again to FIG. 2, diagnostic engine 108 and/or another device in system 100 may populate one or more fields in biological extraction database 200 using expert information, which may be extracted or retrieved from an expert knowledge database 204. An expert knowledge database 204 may include any data structure and/or data store suitable for use as a biological extraction database 200 as described above. Expert knowledge database 204 may include data entries reflecting one or more expert submissions of data such as may have been submitted according to any process described above in reference to FIG. 1, including without limitation by using first graphical user interface 124 and/or second graphical user interface 140. Expert knowledge database may include one or more fields generated by language processing module 128, such as without limitation fields extracted from one or more documents as described above. For instance, and without limitation, one or more categories of physiological data and/or related prognostic labels and/or categories of prognostic labels associated with an element of physiological state data as described above may be stored in generalized from in an expert knowledge database 204 and linked to, entered in, or associated with entries in a biological extraction database 200. Documents may be stored and/or retrieved by diagnostic engine 108 and/or language processing module 128 in and/or from a document database 208; document database 208 may include any data structure and/or data store suitable for use as biological extraction database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

Figure 4:
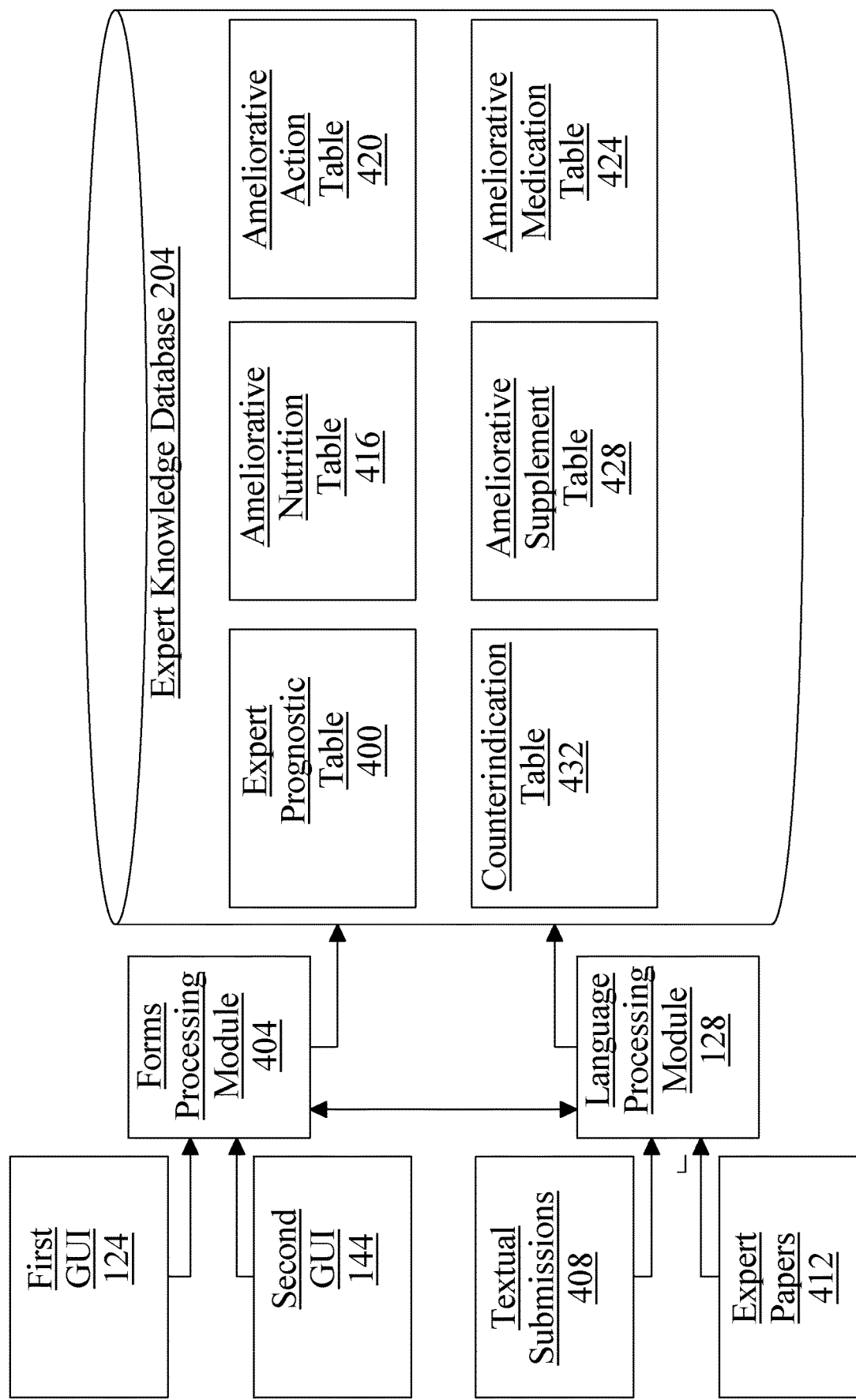
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 200 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert prognostic table 400. Expert prognostic table 400 may be a table relating physiological sample data as described above to prognostic labels; for instance, where an expert has entered data relating a prognostic label to a category of physiological sample data and/or to an element of physiological sample data via first graphical user interface 120 as described above, one or more rows recording such an entry may be inserted in expert prognostic table 400. In an embodiment, a forms processing module 404 may sort data entered in a submission via first graphical user interface 120 by, for instance, sorting data from entries in the first graphical user interface 120 to related categories of data; for instance, data entered in an entry relating in the first graphical user interface 120 to a prognostic label may be sorted into variables and/or data structures for storage of prognostic labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 128 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 128. Data may be extracted from expert papers 412, which may include without limitation publications in medical and/or scientific journals, by language processing module 128 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert prognostic table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, as a further non-limiting example tables listing one or more ameliorative process labels; expert data populating such tables may be provided, without limitation, using any process described above, including entry of data from second graphical user interface 140 via forms processing module 404 and/or language processing module 128, processing of textual submissions 408, or processing of expert papers 412. For instance, and without limitation, an ameliorative nutrition table 416 may list one or more ameliorative processes based on nutritional instructions, and/or links of such one or more ameliorative processes to prognostic labels, as provided by experts according to any method of processing and/or entering expert data as described above. As a further example an ameliorative action table 420 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above. As an additional example, an ameliorative supplement table 424 may list one or more ameliorative processes based on nutritional supplements, such as vitamin pills or the like, and/or links of such one or more ameliorative processes to prognostic labels, as provided by experts according to any method of processing and/or entering expert data as described above. As a further non-limiting example, an ameliorative medication table 428 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above. As an additional example, a counterindication table 432 may list one or more counterindications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like. Tables presented above are presented for exemplary purposes only; persons skilled in the art will be aware of various ways in which data may be organized in expert knowledge database 204 consistently with this disclosure.

Referring again to FIG. 2, a prognostic label database 212, which may be implemented in any manner suitable for implementation of biological extraction database 200, may be used to store prognostic labels used in system 100, including any prognostic labels correlated with elements of physiological data in first training set 112 as described above; prognostic labels may be linked to or refer to entries in biological extraction database 200 to which prognostic labels correspond. Linking may be performed by reference to historical data concerning physiological samples, such as diagnoses, prognoses, and/or other medical conclusions derived from physiological samples in the past; alternatively or additionally, a relationship between a prognostic label and a data entry in biological extraction database 200 may be determined by reference to a record in an expert knowledge database 204 linking a given prognostic label to a given category of physiological sample as described above. Entries in prognostic label database 212 may be associated with one or more categories of prognostic labels as described above, for instance using data stored in and/or extracted from an expert knowledge database 204.

Figure 5:
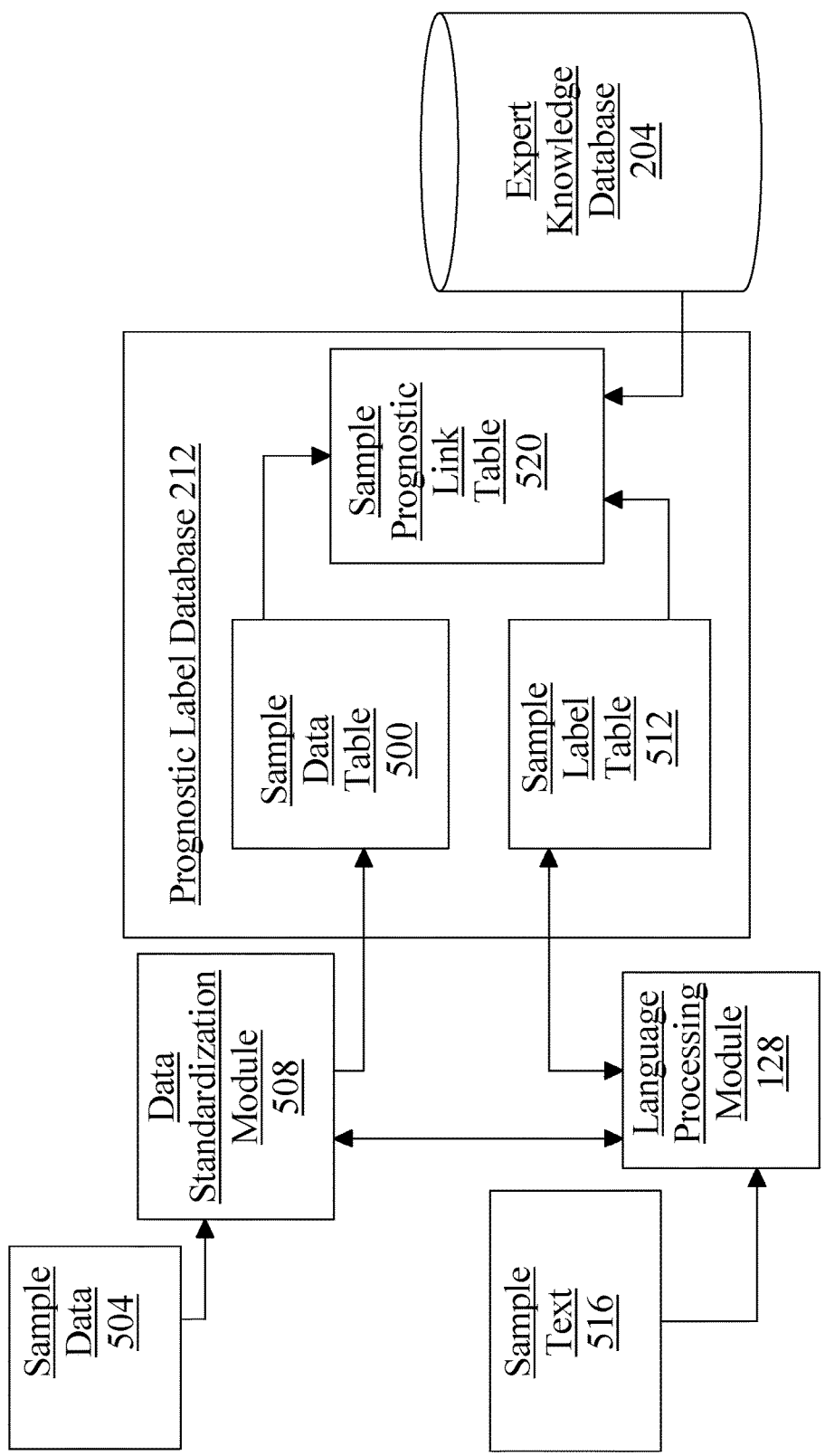
FIG. 5 is a block diagram illustrating an exemplary embodiment of a prognostic label database.

Referring now to FIG. 5, an exemplary embodiment of a prognostic label database 212 is illustrated. Prognostic label database 212 may, as a non-limiting example, organize data stored in the prognostic label database 212 according to one or more database tables. One or more database tables may be linked to one another by, for instance, common column values. For instance, a common column between two tables of prognostic label database 212 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in prognostic label database 212 may include, as a non-limiting example, a sample data table 500. Sample data table 500 may be a table listing sample data, along with, for instance, one or more linking columns to link such data to other information stored in prognostic label database 212. In an embodiment, sample data 504 may be acquired, for instance from biological extraction database 200, in a raw or unsorted form, and may be translated into standard forms, such as standard units of measurement, labels associated with particular physiological data values, or the like; this may be accomplished using a data standardization module 508, which may perform unit conversions. Data standardization module 508 may alternatively or additionally map textual information, such as labels describing values tested for or the like, using language processing module 128 or equivalent components and/or algorithms thereto.

Continuing to refer to FIG. 5, prognostic label database 212 may include a sample label table 512; sample label table 512 may list prognostic labels received with and/or extracted from physiological samples, for instance as received in the form of sample text 516. A language processing module 128 may compare textual information so received to prognostic labels and/or form new prognostic labels according to any suitable process as described above. Sample prognostic link table may combine samples with prognostic labels, as acquired from sample label table and/or expert knowledge database 204; combination may be performed by listing together in rows or by relating indices or common columns of two or more tables to each other. Tables presented above are presented for exemplary purposes only; persons skilled in the art will be aware of various ways in which data may be organized in expert knowledge database 204 consistently with this disclosure.

Referring again to FIG. 2, first training set 112 may be populated by retrieval of one or more records from biological extraction database 200 and/or prognostic label database 212; in an embodiment, entries retrieved from biological extraction database 200 and/or prognostic label database 212 may be filtered and or select via query to match one or more additional elements of information as described above, so as to retrieve a first training set 112 including data belonging to a given cohort, demographic population, or other set, so as to generate outputs as described below that are tailored to a person or persons with regard to whom system 100 classifies physiological samples to prognostic labels as set forth in further detail below. Persons skilled in the art, upon reviewing the entirety of this disclosure, will be aware of various ways in which records may be retrieved from biological extraction database 200 and/or prognostic label database to generate a first training set to reflect individualized group data pertaining to a person of interest in operation of system and/or method, including without limitation a person with regard to whom at least a physiological sample is being evaluated as described in further detail below. Diagnostic engine 108 may alternatively or additionally receive a first training set 112 and store one or more entries in biological extraction database 200 and/or prognostic label database 212 as extracted from elements of first training set 112.

Still referring to FIG. 2, system 100 may include or communicate with an ameliorative process label database 216; an ameliorative process label database 216 may include any data structure and/or datastore suitable for use as a biological extraction database 200 as described above. An ameliorative process label database 216 may include one or more entries listing labels associated with one or more ameliorative processes as described above, including any ameliorative labels correlated with prognostic labels in second training set 132 as described above; ameliorative process labels may be linked to or refer to entries in prognostic label database 212 to which ameliorative process labels correspond. Linking may be performed by reference to historical data concerning prognostic labels, such as therapies, treatments, and/or lifestyle or dietary choices chosen to alleviate conditions associated with prognostic labels in the past; alternatively or additionally, a relationship between an ameliorative process label and a data entry in prognostic label database 212 may be determined by reference to a record in an expert knowledge database 204 linking a given ameliorative process label to a given category of prognostic label as described above. Entries in ameliorative process label database 212 may be associated with one or more categories of prognostic labels as described above, for instance using data stored in and/or extracted from an expert knowledge database 204.

Figure 6:
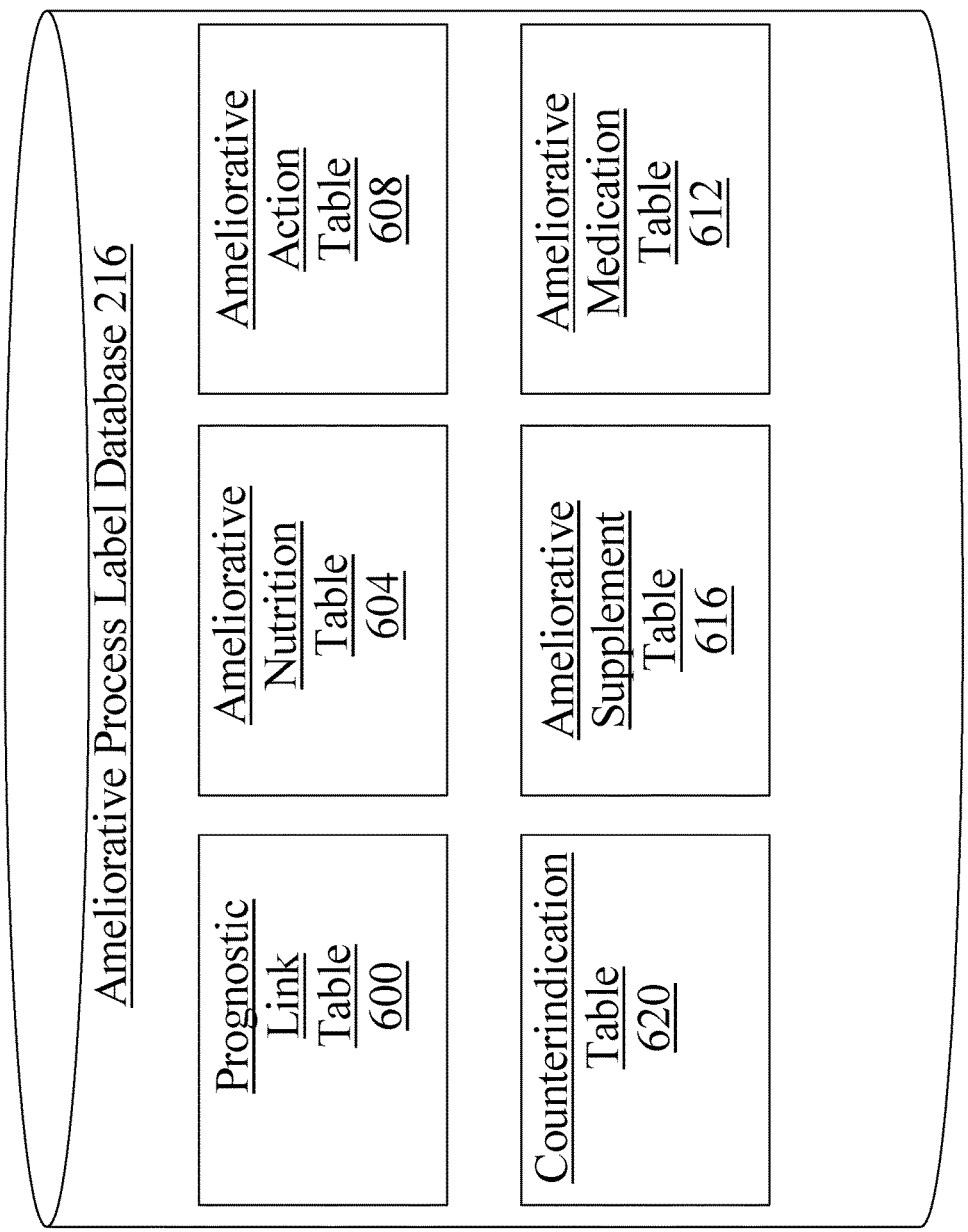
FIG. 6 is a block diagram illustrating an exemplary embodiment of an ameliorative process label database.

Referring now to FIG. 6, an exemplary embodiment of an ameliorative process label database 216 is illustrated. Ameliorative process label database 216 may, as a non-limiting example, organize data stored in the ameliorative process label database 216 according to one or more database tables. One or more database tables may be linked to one another by, for instance, common column values. For instance, a common column between two tables of ameliorative process label database 216 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 6, ameliorative process label database 216 may include a prognostic link table 600; prognostic link table may link ameliorative process data to prognostic label data, using any suitable method for linking data in two or more tables as described above. Ameliorative process label database 216 may include an ameliorative nutrition table 604, which may list one or more ameliorative processes based on nutritional instructions, and/or links of such one or more ameliorative processes to prognostic labels, for instance as provided by experts according to any method of processing and/or entering expert data as described above, and/or using one or more machine-learning processes as set forth in further detail below. As a further example an ameliorative action table 608 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above and/or using one or more machine-learning processes as set forth in further detail below. As an additional example, an ameliorative supplement table 612 may list one or more ameliorative processes based on nutritional supplements, such as vitamin pills or the like, and/or links of such one or more ameliorative processes to prognostic labels, as provided by experts according to any method of processing and/or entering expert data as described above and/or using one or more machine-learning processes as set forth in further detail below. As a further non-limiting example, an ameliorative medication table 616 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above and/or using one or more machine-learning processes as set forth in further detail below. As an additional example, a counter-indication table 620 may list one or more counter-indications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like; this may be acquired using expert submission as described above and/or using one or more machine-learning processes as set forth in further detail below. Tables presented above are presented for exemplary purposes only; persons skilled in the art will be aware of various ways in which data may be organized in ameliorative process database 216 consistently with this disclosure.

Referring again to FIG. 2, second training set 132 may be populated by retrieval of one or more records from prognostic label database 212 and/or ameliorative process label database 216; in an embodiment, entries retrieved from prognostic label database 212 and/or ameliorative process label database 216 may be filtered and or select via query to match one or more additional elements of information as described above, so as to retrieve a second training set 132 including data belonging to a given cohort, demographic population, or other set, so as to generate outputs as described below that are tailored to a person or persons with regard to whom system 100 classifies prognostic labels to ameliorative process labels as set forth in further detail below. Persons skilled in the art, upon reviewing the entirety of this disclosure, will be aware of various ways in which records may be retrieved from prognostic label database 212 and/or ameliorative process label database 216 to generate a second training set 132 to reflect individualized group data pertaining to a person of interest in operation of system and/or method, including without limitation a person with regard to whom at least a physiological sample is being evaluated as described in further detail below. Diagnostic engine 108 may alternatively or additionally receive a second training set 132 and store one or more entries in prognostic label database 212 and/or ameliorative process label database 216 as extracted from elements of second training set 132.

In an embodiment, and still referring to FIG. 2, diagnostic engine 108 may receive an update to one or more elements of data represented in first training set 112 and/or second training set 132, and may perform one or more modifications to first training set 112 and/or second training set 132, or to biological extraction database 200, expert knowledge database 204, prognostic label database 212, and/or ameliorative process label database 216 as a result. For instance, a physiological sample may turn out to have been erroneously recorded; diagnostic engine 108 may remove it from first training set 112, second training set 132, biological extraction database 200, expert knowledge database 204, prognostic label database 212, and/or ameliorative process label database 216 as a result. As a further example, a medical and/or academic paper, or a study on which it was based, may be revoked; diagnostic engine 108 may remove it from first training set 112, second training set 132, biological extraction database 200, expert knowledge database 204, prognostic label database 212, and/or ameliorative process label database 216 as a result. Information provided by an expert may likewise be removed if the expert loses credentials or is revealed to have acted fraudulently.

Continuing to refer to FIG. 2, elements of data first training set 112, second training set 132, biological extraction database 200, expert knowledge database 204, prognostic label database 212, and/or ameliorative process label database 216 may have temporal attributes, such as time-stamps; diagnostic engine 108 may order such elements according to recency, select only elements more recently entered for first training set 112 and/or second training set 132, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Referring again to FIG. 1, diagnostic engine 108 may be configured to record at least a biological extraction. At least a biological extraction may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor 148 may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor 148 may include any electromagnetic sensor, including without limitation electroencephalographic sensors, magnetoencephalographic sensors, electrocardiographic sensors, electromyographic sensors, or the like. At least a sensor 148 may include a temperature sensor.

At least a sensor 148 may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor 148 may detect any hematological parameter including blood oxygen level, pulse rate, heart rate, pulse rhythm, blood sugar, and/or blood pressure. At least a sensor 108 may be configured to detect internal and/or external biomarkers and/or readings. At least a sensor 148 may be a part of system 100 or may be a separate device in communication with system 100.

Still referring to FIG. 1, at least a biological extraction may include any data suitable for use as physiological state data as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

Alternatively or additionally, and with continued reference to FIG. 1, at least a biological extraction may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 1, at least a biological extraction may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure. At least a physiological sample may be added to biological extraction database 200.

With continued reference to FIG. 1, system 100 may include a prognostic label learner 152 operating on the diagnostic engine 108, the prognostic label learner 152 designed and configured to generate the at least a prognostic output as a function of the first training set 112 and the at least a biological extraction. Prognostic label learner 152 may include any hardware and/or software module. Prognostic label learner 152 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 1, prognostic label learner 152 may be designed and configured to generate at least a prognostic output by creating at least a first machine-learning model 152 relating physiological state data 116 to prognostic labels using the first training set 112 and generating the at least a prognostic output using the first machine-learning model 152; at least a first machine-learning model 152 may include one or more models that determine a mathematical relationship between physiological state data 116 and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, machine-learning algorithms may generate prognostic output as a function of a classification of at least a prognostic label. Classification as used herein includes pairing or grouping prognostic labels as a function of a shared commonality. Classification may include for example, groupings, pairings, and/or trends between physiological data and current prognostic label, future prognostic label, and the like. In an embodiment, machine-learning algorithms may examine relationships between a future propensity of a user to develop a condition based on current user physiological data. Machine-learning algorithms may include any and all algorithms as performed by any modules, described herein for prognostic label learner 152. For example, machine-learning algorithms may relate fasting blood glucose readings of a user to user's future propensity to develop diabetes. Machine-learning algorithms may examine precursor condition and future propensity to develop a subsequent disorder. For example, machine-learning algorithms may examine a user diagnosed with chicken pox and user's future propensity to subsequently develop shingles. In yet another non-limiting example, machine-learning algorithms may examine infection with human papillomavirus (HPV) and subsequent cancer diagnosis. Machine-learning algorithms may examine a user's propensity to have recurring attacks of a disease or condition, for example a user with elevated uric acid levels and repeated attacks of gout. Machine-learning algorithms may examine user's genetic predisposition to develop a certain condition or disease. For example, machine-learning algorithms may examine presence of hereditary non-polyposis colorectal cancer (HNPCC) commonly known as lynch syndrome, and subsequent diagnosis of colorectal cancer. In yet another non-limiting example, machine-learning algorithms may examine presence of abnormal squamous cells and/or abnormal glandular cells in the cervix and subsequent development of cervical cancer. Machine-learning algorithms may examine progression of disease state, for example progression of human immunodeficiency virus (HIV) is marked by decline of CD4+T-Cells, with a count below 200 leading to a diagnosis of acquired immunodeficiency syndrome (AIDS). In yet another non-limiting example, progression of diabetes may be marked by increases of hemoglobin A1C levels with a level of 6.5% indicating a diagnosis of diabetes. Machine-learning algorithms may examine progression of disease by certain age groups. For example, progression of Multiple Sclerosis in users between the age of 20-30 as compared to progression of Multiple Sclerosis in users between the age of 70-80. Machine-learning algorithms may be examining progression of aging such as measurements of telomere length and/or oxidative stress levels and chance mortality risk. Machine-learning algorithms may examine development of co-morbid conditions when a disease or conditions is already present. For example, machine-learning algorithms may examine a user diagnosed with depression and subsequent diagnosis of a co-morbid condition such as migraines, generalized anxiety disorder, antisocial personality disorder, agoraphobia, obsessive-compulsive disorder, drug dependence alcohol dependence, and/or panic disorder. Machine-learning algorithms may examine a user's lifetime chance of developing a certain disease or condition, such as a user's lifetime risk of heart disease, Alzheimer's disease, diabetes and the like. Machine-learning algorithms may be grouped and implemented according to any of the methodologies as described below in reference to FIG. 19.

Continuing to refer to FIG. 1, machine-learning algorithm used to generate first machine-learning model 152 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, prognostic label learner 152 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 112; the trained network may then be used to apply detected relationships between elements of physiological state data 116 and prognostic labels.

Figure 7:
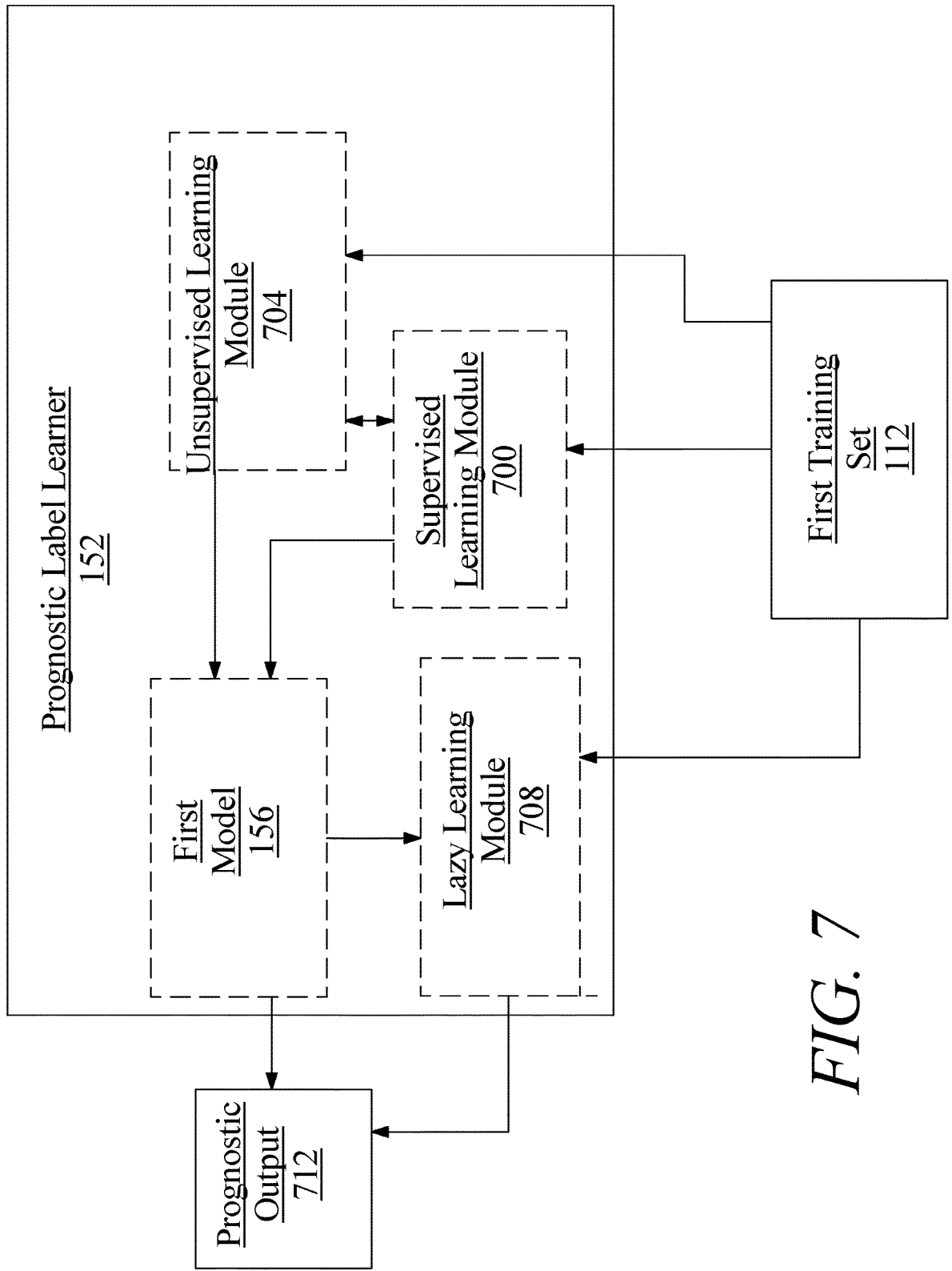
FIG. 7 is a block diagram illustrating an exemplary embodiment of a prognostic label learner and associated system elements.

Referring now to FIG. 7, machine-learning algorithms used by prognostic label learner 152 may include supervised machine-learning algorithms, which may, as a non-limiting example be executed using a supervised learning module 700 executing on diagnostic engine 108 and/or on another computing device in communication with diagnostic engine 108, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data as inputs, prognostic labels as outputs, and a scoring function representing a desired form of relationship to be detected between elements of physiological data and prognostic labels; scoring function may, for instance, seek to maximize the probability that a given element of physiological state data 116 and/or combination of elements of physiological data is associated with a given prognostic label and/or combination of prognostic labels to minimize the probability that a given element of physiological state data 116 and/or combination of elements of physiological state data 116 is not associated with a given prognostic label and/or combination of prognostic labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 112. Persons skilled in the art, upon reviewing the entirety of this disclosure, will be aware of various possible variations of supervised machine learning algorithms that may be used to determine relation between elements of physiological data and prognostic labels. In an embodiment, one or more supervised machine-learning algorithms may be restricted to a particular domain for instance, a supervised machine-learning process may be performed with respect to a given set of parameters and/or categories of parameters that have been suspected to be related to a given set of prognostic labels, and/or are specified as linked to a medical specialty and/or field of medicine covering a particular set of prognostic labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between physiological data and prognostic labels.

Referring again to FIG. 1, machine-learning algorithms may include unsupervised processes; unsupervised processes may, as a non-limiting example, be executed by an unsupervised learning module 704 executing on diagnostic engine 108 and/or on another computing device in communication with diagnostic engine 108, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, prognostic label learner 152 and/or diagnostic engine 108 may perform an unsupervised machine learning process on first training set 112, which may cluster data of first training set 112 according to detected relationships between elements of the first training set 112, including without limitation correlations of elements of physiological state data 116 to each other and correlations of prognostic labels to each other; such relations may then be combined with supervised machine learning results to add new criteria for prognostic label learner 152 to apply in relating physiological state data 116 to prognostic labels. As a non-limiting, illustrative example, an unsupervised process may determine that a first element of physiological data acquired in a blood test correlates closely with a second element of physiological data, where the first element has been linked via supervised learning processes to a given prognostic label, but the second has not; for instance, the second element may not have been defined as an input for the supervised learning process, or may pertain to a domain outside of a domain limitation for the supervised learning process. Continuing the example a close correlation between first element of physiological state data 116 and second element of physiological state data 116 may indicate that the second element is also a good predictor for the prognostic label; second element may be included in a new supervised process to derive a relationship or may be used as a synonym or proxy for the first physiological element by prognostic label learner 152.

Still referring to FIG. 1, diagnostic engine 108 and/or prognostic label learner 152 may detect further significant categories of physiological data, relationships of such categories to prognostic labels, and/or categories of prognostic labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, prognostic label learner 152 and/or diagnostic engine 108 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 1, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 1, prognostic label learner 152 may alternatively or additionally be designed and configured to generate at least a prognostic output by executing a lazy learning process as a function of the first training set 112 and the at least a biological extraction; lazy learning processes may be performed by a lazy learning module 708 executing on diagnostic engine 108 and/or on another computing device in communication with diagnostic engine 108, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a prognostic label associated with biological extraction, using first training set 112. As a non-limiting example, an initial heuristic may include a ranking of prognostic labels according to relation to a test type of at least a biological extraction, one or more categories of physiological data identified in test type of at least a biological extraction, and/or one or more values detected in at least a biological extraction; ranking may include, without limitation, ranking according to significance scores of associations between elements of physiological data and prognostic labels, for instance as calculated as described above. Heuristic may include selecting some number of highest-ranking associations and/or prognostic labels. Prognostic label learner 152 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below.

In an embodiment, and continuing to refer to FIG. 1, prognostic label learner 152 may generate a plurality of prognostic labels having different implications for a particular person. For instance, where the at least a physiological sample includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, prognostic label learner 152 and/or diagnostic engine 108 may perform additional processes to resolve ambiguity. Processes may include presenting multiple possible results to a medical practitioner, informing the medical practitioner that one or more follow-up tests and/or physiological samples are needed to further determine a more definite prognostic label. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, prognostic label learner 152 and/or diagnostic engine 108 may operate a further algorithm to determine which of the multiple outputs is most likely to be correct; algorithm may include use of an additional supervised and/or unsupervised model. Alternatively or additionally, prognostic label learner 152 may perform one or more lazy learning processes using a more comprehensive set of user data to identify a more probably correct result of the multiple results. Results may be presented and/or retained with rankings, for instance to advise a medical professional of the relative probabilities of various prognostic labels being correct; alternatively or additionally, prognostic labels associated with a probability of correctness below a given threshold and/or prognostic labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of prognostic labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of prognostic labels on a list of multiple prognostic labels, and/or to eliminate some labels from such a list. Prognostic output 712 may be provided to user output device as described in further detail below.

Still referring to FIG. 1, diagnostic engine 108 includes an ameliorative process label learner 160 operating on the diagnostic engine 108, the ameliorative process label learner 160 designed and configured to generate the at least an ameliorative output as a function of the second training set 132 and the at least a prognostic output. Ameliorative process label learner 160 may include any hardware or software module suitable for use as a prognostic label learner 152 as described above. Ameliorative process label learner 160 is a machine-learning module as described above; ameliorative process label learner 160 may perform any machine-learning process or combination of processes suitable for use by a prognostic label learner 152 as described above. For instance, and without limitation, and ameliorative process label learner 160 may be configured to create a second machine-learning model 160 relating prognostic labels to ameliorative labels using the second training set 132 and generate the at least an ameliorative output using the second machine-learning model 160; second machine-learning model 160 may be generated according to any process, process steps, or combination of processes and/or process steps suitable for creation of first machine learning model. In an embodiment, ameliorative process label learner 160 may use data from first training set 112 as well as data from second training set 132; for instance, ameliorative process label learner 160 may use lazy learning and/or model generation to determine relationships between elements of physiological data, in combination with or instead of prognostic labels, and ameliorative labels. Where ameliorative process label learner 160 determines relationships between elements of physiological data and ameliorative labels directly, this may determine relationships between prognostic labels and ameliorative labels as well owing to the existence of relationships determined by prognostic label learner 152.

Figure 8:
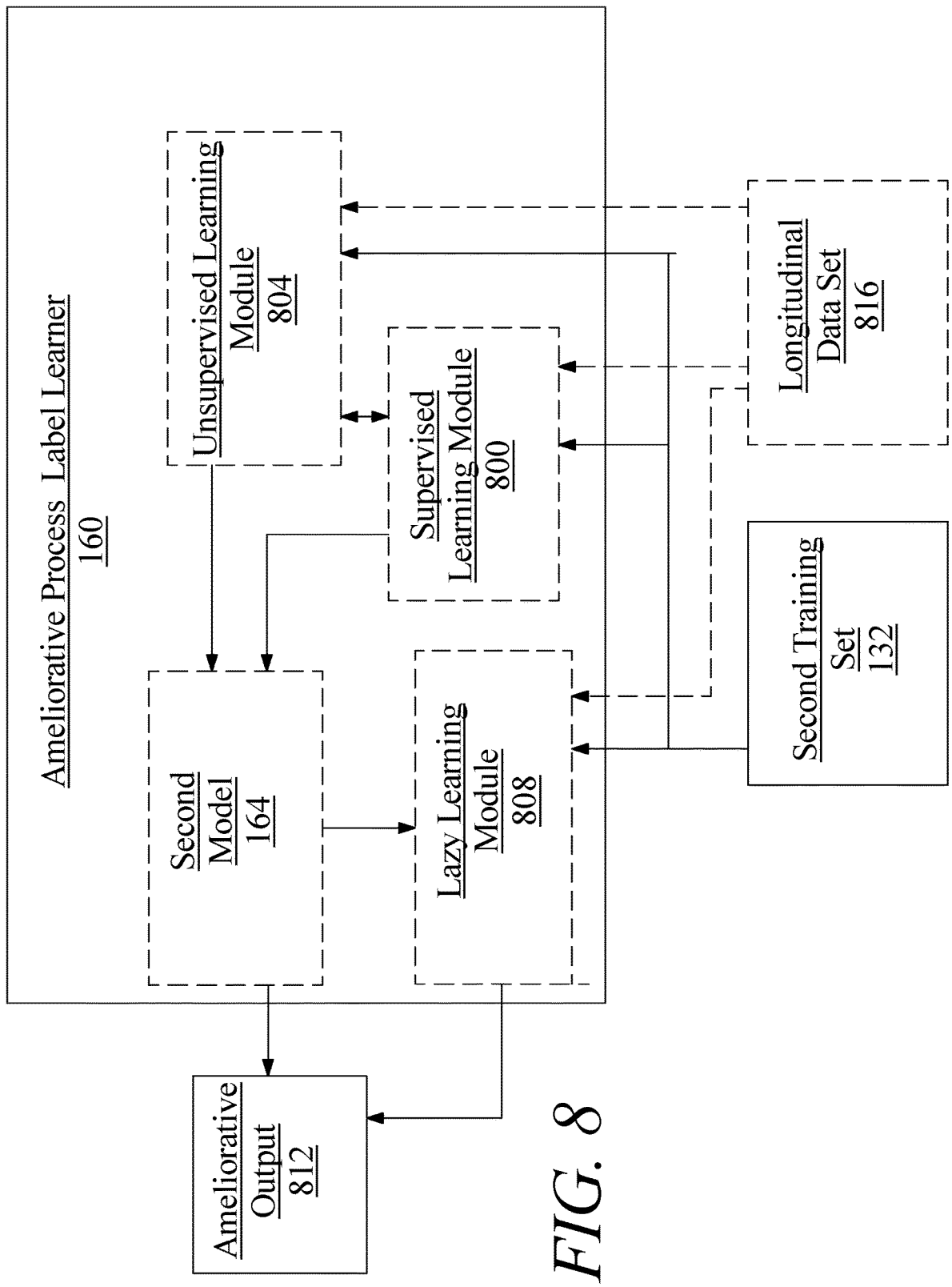
FIG. 8 is a block diagram illustrating an exemplary embodiment of an ameliorative process label learner and associated system elements.

Referring now to FIG. 8, ameliorative process label learner 160 may be configured to perform one or more supervised learning processes, as described above; supervised learning processes may be performed by a supervised learning module 800 executing on diagnostic engine 108 and/or on another computing device in communication with diagnostic engine 108, which may include any hardware or software module. For instance, a supervised learning algorithm may use prognostic labels as inputs, ameliorative labels as outputs, and a scoring function representing a desired form of relationship to be detected between prognostic labels and ameliorative labels; scoring function may, for instance, seek to maximize the probability that a given prognostic label and/or combination of prognostic labels is associated with a given ameliorative label and/or combination of ameliorative labels to minimize the probability that a given prognostic label and/or combination of prognostic labels is not associated with a given ameliorative label and/or combination of ameliorative labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of ameliorative labels, for instance because the ameliorative processes corresponding to the set of ameliorative labels are hypothesized or suspected to have an ameliorative effect on conditions represented by the prognostic labels, and/or are specified as linked to a medical specialty and/or field of medicine covering a particular set of prognostic labels and/or ameliorative labels. As a non-limiting example, a particular set prognostic labels corresponding to a set of cardiovascular conditions may be typically treated by cardiologists, and a supervised machine-learning process may be performed to relate those prognostic labels to ameliorative labels associated with various treatment options, medications, and/or lifestyle changes.

With continued reference to FIG. 8, ameliorative process label learner 160 may perform one or more unsupervised machine-learning processes as described above; unsupervised processes may be performed by an unsupervised learning module 804 executing on diagnostic engine 108 and/or on another computing device in communication with diagnostic engine 108, which may include any hardware or software module. For instance, and without limitation, ameliorative process label learner 160 and/or diagnostic engine 108 may perform an unsupervised machine learning process on second training set 132, which may cluster data of second training set 132 according to detected relationships between elements of the second training set 132, including without limitation correlations of prognostic labels to each other and correlations of ameliorative labels to each other; such relations may then be combined with supervised machine learning results to add new criteria for ameliorative process label learner 160 to apply in relating prognostic labels to ameliorative labels. As a non-limiting, illustrative example, an unsupervised process may determine that a first prognostic label 120 correlates closely with a second prognostic label 136, where the first prognostic label 120 has been linked via supervised learning processes to a given ameliorative label, but the second has not; for instance, the second prognostic label 136 may not have been defined as an input for the supervised learning process, or may pertain to a domain outside of a domain limitation for the supervised learning process. Continuing the example, a close correlation between first prognostic label 120 and second prognostic label 136 may indicate that the second prognostic label 136 is also a good match for the ameliorative label; second prognostic label 136 may be included in a new supervised process to derive a relationship or may be used as a synonym or proxy for the first prognostic label 120 by ameliorative process label learner 160. Unsupervised processes performed by ameliorative process label learner 160 may be subjected to any domain limitations suitable for unsupervised processes performed by prognostic label learner 152 as described above.

Still referring to FIG. 8, diagnostic engine 108 and/or ameliorative process label learner 160 may detect further significant categories of prognostic labels, relationships of such categories to ameliorative labels, and/or categories of ameliorative labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, ameliorative process label learner 160 and/or diagnostic engine 108 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 8, ameliorative labels may be generated based on classification of the at least a prognostic output. Classification as used herein includes pairing or grouping prognostic outputs as a function of some shared commonality. Prognostic outputs may be grouped with certain endocrine disorders such as diabetes, metabolic syndrome, and/or pre-diabetes which may generate an ameliorative label associated with a physical exercise recommendation that may include aerobic exercises such as running, brisk walking, cycling, and/or swimming in an attempt to reduce elevated blood sugar levels in patients with such endocrine disorders. Prognostic outputs grouped with certain alarm conditions such as chest pains, shortness of breath, cold sweat, and sudden dizziness may generate an ameliorative label associated with medical tests, diagnostics, and/or procedures for a suspected myocardial infarction such as an electrocardiogram (EKG), measurement of serum troponin levels, complete blood count (CBC), chest x-ray, echocardiogram, cardiac CT, cardiac MRI, and/or coronary catheterization. Ameliorative label may be generated based on groupings such as severity of prognostic output. For example, a user who presents with mild chest pain and some indigestion may be grouped to a category of prognostic labels that is serious but not alarming and may generate an ameliorative label that includes a blood test for troponin levels to rule out a potential myocardial infarction. A user who presents with crushing chest pain, tingling down one or both arms, shortness of breath, and cold and clammy skin may be grouped into a category of alarm so as to generate an ameliorative label that includes a cardiac CT or cardiac MRI to see if user is suffering from some type of coronary occlusion and may be a candidate for a possible coronary catheterization. In yet another non-limiting example, ameliorative label may be generated as a function of severity and/or progression of prognostic output. For example, a prognostic label that includes a diagnosis of hypothyroidism as evidenced by a thyroid stimulating level (TSH) of 6.0 (normal range is 1.4-5.5) may generate an ameliorative label that includes 150 mcg per day of iodine supplementation to lower TSH within normal limits due to mild TSH elevation and/or mild progression of hypothyroidism. A prognostic output that includes a diagnosis of hypothyroidism as evidenced by a TSH of 15.0 may generate an ameliorative label that includes 300 mcg per day of iodine supplementation as well as a prescription for a T-4 containing medication such as Synthroid and a T-3 containing medication such as Cytomel due to the more severe progression of hypothyroidism. Classification of at least a prognostic output may include staging of a prognostic label. Staging may include dividing a disease state or condition into categories on a spectrum of disease progression and symptomology. For example, a user with a prognostic output that indicates peri-menopause as evidenced by increasing prevalence of hot flashes may generate an ameliorative label that includes a recommendation for supplementation with black cohosh, while a user with a prognostic output that indicates progression to menopause as evidenced by persistent hot flashes, night sweats, absence of menstruation, dry hair, and fatigue may generate an ameliorative label that contains recommendations for supplementation with bio-identical hormone replacement therapy such as estrone (E1), estradiol (E2), estriol (E3), progesterone, testosterone, dehydroepiandrosterone (DHEA), and/or pregnenolone. In yet another non-limiting example, early stage of a disease such as Alzheimer's disease as demonstrated by mild cognitive impairment may generate an ameliorative label that includes no recommended medical treatment except for watchful waiting. However, advanced Alzheimer's disease may warrant an ameliorative label that includes medical intervention and may require a prescription medication. Ameliorative label may be generated by any of the methodologies as described below in reference to FIG. 19.

Continuing to view FIG. 8, ameliorative process label learner 160 may be configured to perform a lazy learning process as a function of the second training set 132 and the at least a prognostic output to produce the at least an ameliorative output; a lazy learning process may include any lazy learning process as described above regarding prognostic label learner 152. Lazy learning processes may be performed by a lazy learning module 808 executing on diagnostic engine 108 and/or on another computing device in communication with diagnostic engine 108, which may include any hardware or software module. Ameliorative output 812 may be provided to a user output device as described in further detail below.

In an embodiment, and still referring to FIG. 8, ameliorative process label learner 160 may generate a plurality of ameliorative labels having different implications for a particular person. For instance, where a prognostic label indicates that a person has a magnesium deficiency, various dietary choices may be generated as ameliorative labels associated with correcting the deficiency, such as ameliorative labels associated with consumption of almonds, spinach, and/or dark chocolate, as well as ameliorative labels associated with consumption of magnesium supplements. In such a situation, ameliorative process label learner 160 and/or diagnostic engine 108 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine learning steps. For instance, ameliorative process label learner 160 may perform one or more lazy learning processes using a more comprehensive set of user data to identify a more probably correct result of the multiple results. Results may be presented and/or retained with rankings, for instance to advise a medical professional of the relative probabilities of various ameliorative labels being correct or ideal choices for a given person; alternatively or additionally, ameliorative labels associated with a probability of success or suitability below a given threshold and/or ameliorative labels contradicting results of the additional process, may be eliminated. As a non-limiting example, an additional process may reveal that a person is allergic to tree nuts, and consumption of almonds may be eliminated as an ameliorative label to be presented.

Continuing to refer to FIG. 8, ameliorative process label learner 160 may be designed and configured to generate further training data and/or to generate outputs using longitudinal data 816. As used herein, longitudinal data 816 may include a temporally ordered series of data concerning the same person, or the same cohort of persons; for instance, longitudinal data 816 may describe a series of blood samples taken one day or one month apart over the course of a year. Longitudinal data 816 may related to a series of samples tracking response of one or more elements of physiological data recorded regarding a person undergoing one or more ameliorative processes linked to one or more ameliorative process labels. Ameliorative process label learner 160 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given ameliorative process over time on a physiological parameter. Functions may be compared to each other to rank ameliorative processes; for instance, an ameliorative process associated with a steeper slope in curve representing improvement in a physiological data element, and/or a shallower slope in a curve representing a slower decline, may be ranked higher than an ameliorative process associated with a less steep slope for an improvement curve or a steeper slope for a curve marking a decline. Ameliorative processes associated with a curve and/or terminal data point representing a value that does not associate with a previously detected prognostic label may be ranked higher than one that is not so associated. Information obtained by analysis of longitudinal data 816 may be added to ameliorative process database and/or second training set.

Referring again to FIG. 1, system 100 may include a plan generation module 168 operating on the at least a server 104. Plan generator module 168 may include any suitable hardware or hardware module. In an embodiment, plan generator module 168 is designed and configured to generate a comprehensive instruction set 172 associated with the user based on the diagnostic output. In an embodiment, comprehensive instruction set 172 is a data structure containing instructions to be provided to the user to explain the user's current prognostic status, as reflected by one or more prognostic outputs and provide the user with a plan based on the at least an ameliorative output, to achieve that. In an embodiment, comprehensive instruction set 172 may be generated based on at least an informed advisor output. Comprehensive instruction set 172 may include but is not limited to a program, strategy, summary, recommendation, or any other type of interactive platform that may be configured to comprise information associated with the user, an applicable verified external source, and one or more outputs derived from the analyses performed on the extraction from the user. Comprehensive instruction set 172 may describe to a user a future prognostic status to aspire to. In an embodiment, plan generation module 168 is configured to receive at least an element of user data and filter the diagnostic output using the at least an element of user data.

Figure 9:
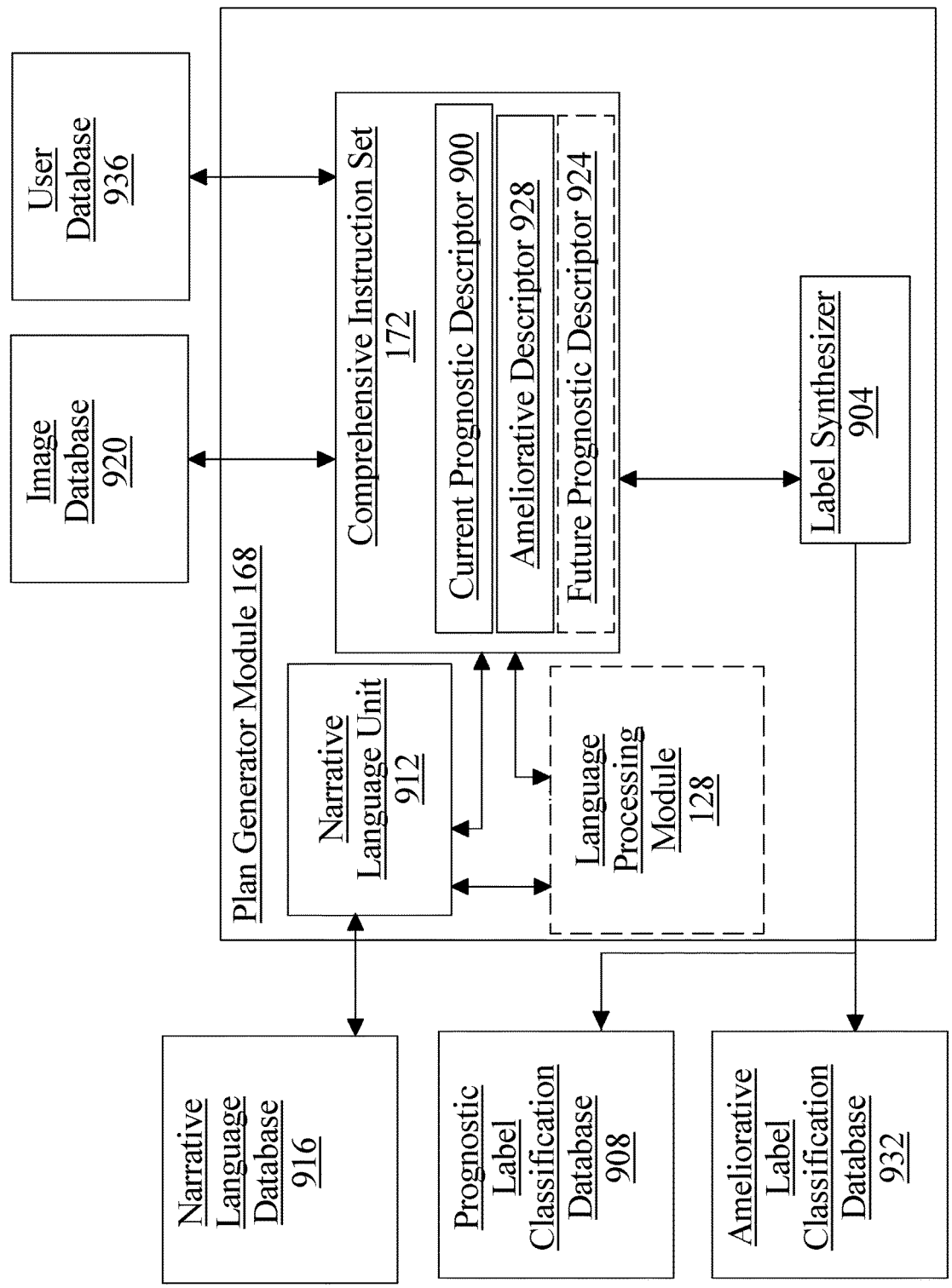
FIG. 9 is a block diagram illustrating an exemplary embodiment of a plan generator module and associated system elements.

Referring now to FIG. 9, an exemplary embodiment of a plan generator module 168 is illustrated. Comprehensive instruction set 172 includes at least a current prognostic descriptor 900 which as used in this disclosure is an element of data describing a current prognostic status based on at least one prognostic output. Plan generator module 168 may produce at least a current prognostic descriptor 900 using at least a prognostic output. In an embodiment, plan generator module 168 may include a label synthesizer 904. Label synthesizer 904 may include any suitable software or hardware module. In an embodiment, label synthesizer 904 may be designed and configured to combine a plurality of labels in at least a prognostic output together to provide maximally efficient data presentation. Combination of labels together may include elimination of duplicate information. For instance, label synthesizer 904 and/or at least a server 104 may be designed and configure to determine a first prognostic label of the at least a prognostic label is a duplicate of a second prognostic label of the at least a prognostic label and eliminate the first prognostic label. Determination that a first prognostic label is a duplicate of a second prognostic label may include determining that the first prognostic label is identical to the second prognostic label; for instance, a prognostic label generated from test data presented in one biological extraction of at least a biological extraction may be the same as a prognostic label generated from test data presented in a second biological extraction of at least a biological extraction. As a further non-limiting example, a first prognostic label may be synonymous with a second prognostic label, where detection of synonymous labels may be performed, without limitation, by a language processing module 128 as described above.

Continuing to refer to FIG. 9, label synthesizer 904 may group prognostic labels according to one or more classification systems relating the prognostic labels to each other. For instance, plan generator module 168 and/or label synthesizer 904 may be configured to determine that a first prognostic label of the at least a prognostic label and a second prognostic label of the at least a prognostic label belong to a shared category. A shared category may be a category of conditions or tendencies toward a future condition to which each of first prognostic label and second prognostic label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with prognostic labels as well. A given prognostic label may belong to a plurality of overlapping categories. Plan generator module 168 may be configured to add a category label associated with a shared category to comprehensive instruction set 172, where addition of the label may include addition of the label and/or a datum linked to the label, such as a textual or narrative description. In an embodiment, relationships between prognostic labels and categories may be retrieved from a prognostic label classification database 908, for instance by generating a query using one or more prognostic labels of at least a prognostic output, entering the query, and receiving one or more categories matching the query from the prognostic label classification database 908.

Figure 10:
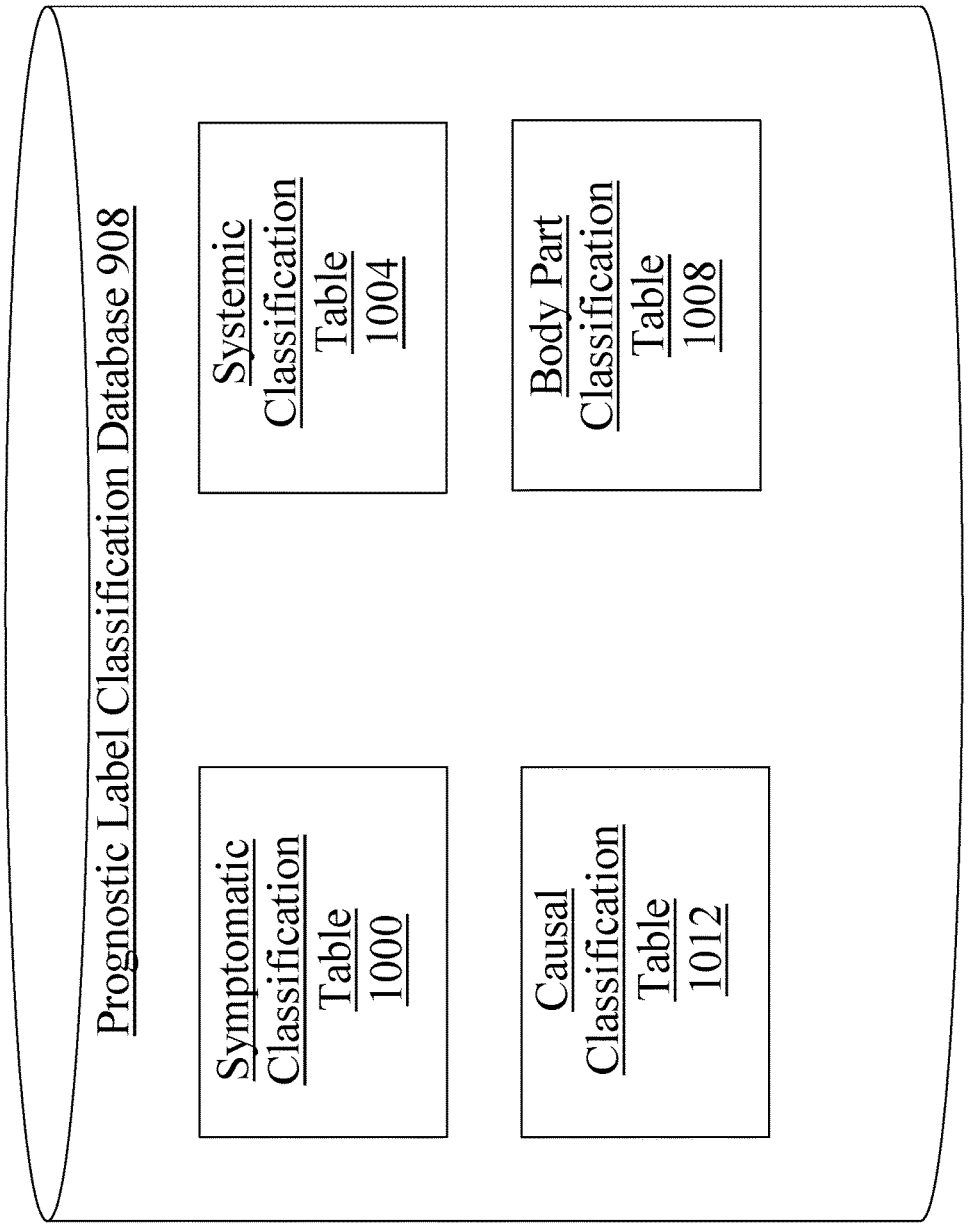
FIG. 10 is a block diagram illustrating an exemplary embodiment of a prognostic label classification database.

Referring now to FIG. 10, an exemplary embodiment of a prognostic label classification database 908 is illustrated. Prognostic label classification database 908 may be implemented as any database and/or datastore suitable for use as biological extraction database 300 as described above. One or more database tables in prognostic label classification database 908 may include, without limitation, a symptomatic classification table 1000; symptomatic classification table 1000 may relate each prognostic label to one or more categories of symptoms associated with that prognostic label. As a non-limiting example, symptomatic classification table 1000 may include records indicating that each of lactose intolerance and gluten sensitivity results in symptoms including gas buildup, bloating, and abdominal pain. One or more database tables in prognostic label classification database 908 may include, without limitation, a systemic classification table 1004; systemic classification table 1004 may relate each prognostic label to one or more systems associated with that prognostic label. As a non-limiting example, systemic classification table 1004 may include records indicating each of lactose intolerance and gluten sensitivity affects the digestive system; two digestive sensitivities linked to allergic or other immune responses may additionally be linked in systemic classification table 1004 to the immune system. One or more database tables in prognostic label classification database 908 may include, without limitation, a body part classification table 1008; body part classification table 1008 may relate each prognostic label to one or more body parts associated with that prognostic label. As a non-limiting example, body part classification table 1008 may include records indicating each of psoriasis and rosacea affects the skin of a person. One or more database tables in prognostic label classification database 908 may include, without limitation, a causal classification table 1112; causal classification table 1112 may relate each prognostic label to one or more causes associated with that prognostic label. As a non-limiting example, causal classification table 1112 may include records indicating each of type 2 diabetes and hypertension may have obesity as a cause. The above-described tables, and entries therein, are provided solely for exemplary purposes. Persons skilled in the art, upon reviewing the entirety of this disclosure, will be aware of various additional examples for tables and/or relationships that may be included or recorded in prognostic classification table consistently with this disclosure.

Referring again to FIG. 9, plan generator module 168 may be configured to generate current prognostic descriptor 900 by converting one or more prognostic labels into narrative language. As a non-limiting example, plan generator module 168 may include a narrative language unit 912, which may be configured to determine an element of narrative language associated with at least a prognostic label and include the element of narrative language in current prognostic label descriptor. Narrative language unit 912 may implement this, without limitation, by using a language processing module 128 to detect one or more associations between prognostic labels, or lists of prognostic labels, and phrases and/or statements of narrative language. Alternatively or additionally, narrative language unit 912 may retrieve one or more elements of narrative language from a narrative language database 916, which may contain one or more tables associating prognostic labels and/or groups of prognostic labels with words, sentences, and/or phrases of narrative language. One or more elements of narrative language may be included in comprehensive instruction set 172, for instance for display to a user as text describing a current prognostic status of the user. Current prognostic descriptor 900 may further include one or more images; one or more images may be retrieved by plan generator module 168 from an image database 920, which may contain one or more tables associating prognostic labels, groups of prognostic labels, current prognostic descriptors 1000, or the like with one or more images.

With continued reference to FIG. 9, comprehensive instruction set 172 may include one or more follow-up suggestions, which may include, without limitation, suggestions for acquisition of an additional biological extraction; in an embodiment, additional biological extraction may be provided to diagnostic engine 108, which may trigger repetition of one or more processes as described above, including without limitation generation of prognostic output, refinement or elimination of ambiguous prognostic labels of prognostic output, generation of ameliorative output, and/or refinement or elimination of ambiguous ameliorative labels of ameliorative output. For instance, where a pegboard test result suggests possible diagnoses of Parkinson's disease, Huntington's disease, ALS, and MS as described above, follow-up suggestions may include suggestions to perform endocrinal tests, genetic tests, and/or electromyographic tests; results of such tests may eliminate one or more of the possible diagnoses, such that a subsequently displayed output only lists conditions that have not been eliminated by the follow-up test. Follow-up tests may include any receipt of any biological extraction as described above.

With continued reference to FIG. 9, comprehensive instruction set may include one or more elements of contextual information, including without limitation any patient medical history such as current lab results, a current reason for visiting a medical professional, current status of one or more currently implemented treatment plans, biographical information concerning the patient, and the like. One or more elements of contextual information may include goals a patient wishes to achieve with a medical visit or session, and/or as result of interaction with diagnostic engine 108. Contextual information may include one or more questions a patient wishes to have answered in a medical visit and/or session, and/or as a result of interaction with diagnostic engine 108. Contextual information may include one or more questions to ask a patient. Persons skilled in the art, upon reviewing the entirety of this disclosure, will be aware of various forms of contextual information that may be included, consistently with this disclosure.

With continued reference to FIG. 9, comprehensive instruction set 172 may include at least a future prognostic descriptor 924. As used herein, a future prognostic descriptor 924 is an element of data describing a future prognostic status based on at least one prognostic output, which may include without limitation a desired further prognostic status. In an embodiment, future prognostic descriptor 924 may include any element suitable for inclusion in current prognostic descriptor 900. Future prognostic descriptor 924 may be generated using any processes, modules, and/or components suitable for generation of current prognostic descriptor 900 as described above.

Still referring to FIG. 9, comprehensive instruction set 172 includes at least an ameliorative process descriptor 1028, which as defined in this disclosure an element of data describing one or more ameliorative processes to be followed based on at least one ameliorative output; at least an ameliorative process descriptor 1028 may include descriptors for ameliorative processes usable to achieve future prognostic descriptor 924. Plan generator module 168 may produce at least an ameliorative process descriptor 1028 using at least a prognostic output. In an embodiment, label synthesizer 904 may be designed and configured to combine a plurality of labels in at least an ameliorative output together to provide maximally efficient data presentation. Combination of labels together may include elimination of duplicate information. For instance, label synthesizer 904 and/or at least a server 104 may be designed and configure to determine a first ameliorative label of the at least an ameliorative label is a duplicate of a second ameliorative label of the at least an ameliorative label and eliminate the first ameliorative label. Determination that a first ameliorative label is a duplicate of a second ameliorative label may include determining that the first ameliorative label is identical to the second ameliorative label; for instance, a ameliorative label generated from test data presented in one biological extraction of at least a biological extraction may be the same as a ameliorative label generated from test data presented in a second biological extraction of at least a biological extraction. As a further non-limiting example, a first ameliorative label may be synonymous with a second ameliorative label, where detection of synonymous labels may be performed, without limitation, by a language processing module 128 as described above.

Continuing to refer to FIG. 9, label synthesizer 904 may group ameliorative labels according to one or more classification systems relating the ameliorative labels to each other. For instance, plan generator module 168 and/or label synthesizer 904 may be configured to determine that a first ameliorative label of the at least an ameliorative label and a second ameliorative label of the at least an ameliorative label belong to a shared category. A shared category may be a category of conditions or tendencies toward a future condition to which each of first ameliorative label and second ameliorative label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with ameliorative labels as well. A given ameliorative label may belong to a plurality of overlapping categories. Plan generator module 168 may be configured to add a category label associated with a shared category to comprehensive instruction set 172, where addition of the label may include addition of the label and/or a datum linked to the label, such as a textual or narrative description. In an embodiment, relationships between ameliorative labels and categories may be retrieved from an ameliorative label classification database 932, for instance by generating a query using one or more ameliorative labels of at least an ameliorative output, entering the query, and receiving one or more categories matching the query from the ameliorative label classification database 932.

Figure 11:
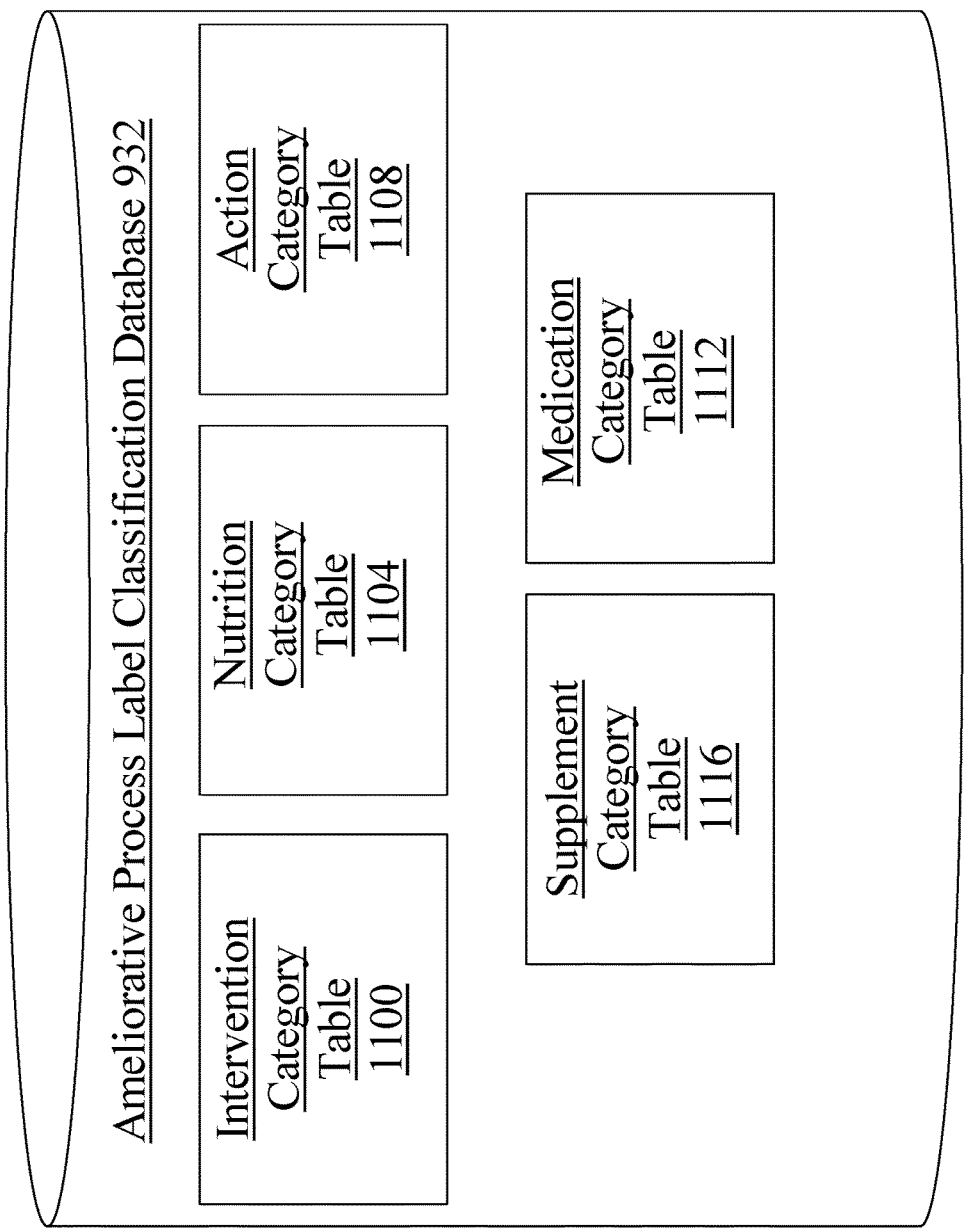
FIG. 11 is a block diagram illustrating an exemplary embodiment of an ameliorative process label classification database.

Referring now to FIG. 11, an exemplary embodiment of an ameliorative label classification database 932 is illustrated. Ameliorative label classification database 932 may be implemented as any database and/or datastore suitable for use as biological extraction database 300 as described above. One or more database tables in ameliorative label classification database 932 may include, without limitation, an intervention category table 1100; intervention 1200 may relate each ameliorative label to one or more categories associated with that ameliorative label. As a non-limiting example, intervention category table 1100 may include records indicating that each of a plan to consume a given quantity of almonds and a plan to consume less meat maps to a category of nutritional instruction, while a plan to jog for 30 minutes per day maps to a category of activity. One or more database tables in ameliorative label classification database 932 may include, without limitation, a nutrition category table 1104; nutrition category table 1104 may relate each ameliorative label pertaining to nutrition to one or more categories associated with that ameliorative label. As a non-limiting example, nutrition category table 1104 may include records indicating that each of a plan to consume more almonds and a plan to consume more walnuts qualifies as a plan to consume more nuts, as well as a plan to consume more protein. One or more database tables in ameliorative label classification database 932 may include, without limitation, an action category table 1108; action category table 1108 may relate each ameliorative label pertaining to an action to one or more categories associated with that ameliorative label. As a non-limiting example, action category table 1108 may include records indicating that each of a plan jog for 30 minutes a day and a plan to perform a certain number of sit-ups per day qualifies as an exercise plan. One or more database tables in ameliorative label classification database 932 may include, without limitation, a medication category table 1112; medication category table 1112 may relate each ameliorative label associated with a medication to one or more categories associated with that ameliorative label. As a non-limiting example, medication category table 1112 may include records indicating that each of a plan to take an antihistamine and a plan to take an anti-inflammatory steroid belongs to a category of allergy medications. One or more database tables in ameliorative label classification database 932 may include, without limitation, a supplement category table 1116; supplement category table 1116 may relate each ameliorative label pertaining to a supplement to one or more categories associated with that ameliorative label. As a non-limiting example, supplement category table 1116 may include records indicating that each of a plan to consume a calcium supplement and a plan to consume a vitamin D supplement corresponds to a category of supplements to aid in bone density. Ameliorative labels may be mapped to each of nutrition category table 1104, action category table 1108, supplement category table 1116, and medication category table 1112 using intervention category table 1100. The above-described tables, and entries therein, are provided solely for exemplary purposes. Persons skilled in the art, upon reviewing the entirety of this disclosure, will be aware of various additional examples for tables and/or relationships that may be included or recorded in ameliorative classification table consistently with this disclosure.

Referring again to FIG. 9, plan generator module 168 may be configured to generate ameliorative process descriptor 1028 by converting one or more ameliorative labels into narrative language. As a non-limiting example, plan generator module 168 may include a narrative language unit 912, which may be configured to determine an element of narrative language associated with at least an ameliorative label and include the element of narrative language in current ameliorative label descriptor. Narrative language unit 912 may implement this, without limitation, by using a language processing module 128 to detect one or more associations between ameliorative labels, or lists of ameliorative labels, and phrases and/or statements of narrative language. Alternatively or additionally, narrative language unit 912 may retrieve one or more elements of narrative language from narrative language database 916, which may contain one or more tables associating ameliorative labels and/or groups of ameliorative labels with words, sentences, and/or phrases of narrative language. One or more elements of narrative language may be included in comprehensive instruction set 172, for instance for display to a user as text describing a current ameliorative status of the user. Ameliorative process descriptor 1028 may further include one or more images; one or more images may be retrieved by plan generator module 168 from an image database 920, which may contain one or more tables associating ameliorative labels, groups of ameliorative labels, ameliorative process descriptors 1028, or the like with one or more images.

Figure 12:
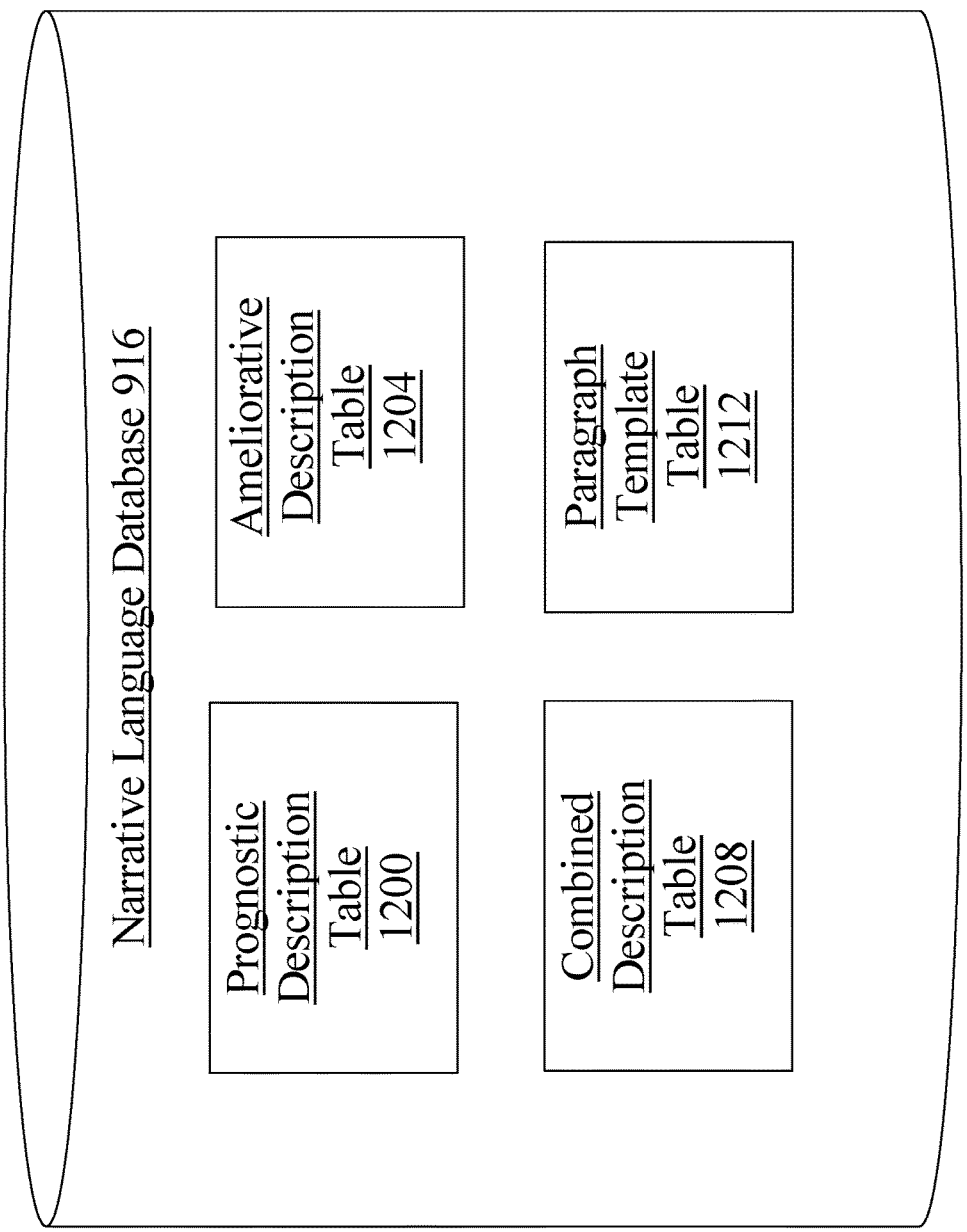
FIG. 12 is a block diagram illustrating an exemplary embodiment of a narrative language database.

Referring now to FIG. 12, and exemplary embodiment of a narrative language database 916 is illustrated. Narrative language database 916 may be implemented as any database and/or datastore suitable for use as biological extraction database 300 as described above. One or more database tables in narrative language database 916 may include, without limitation, a prognostic description table 1200, which may link prognostic labels to narrative descriptions associated with prognostic labels. One or more database tables in narrative language database 916 may include, without limitation, an ameliorative description table 1204, which may link ameliorative process labels to narrative descriptions associated with ameliorative process labels. One or more database tables in narrative language database 916 may include, without limitation, a combined description table 1208, which may link combinations of prognostic labels and ameliorative labels to narrative descriptions associated with the combinations. One or more database tables in narrative language database 916 may include, without limitation, a paragraph template table 1212, which may contain one or more templates of paragraphs, pages, reports, or the like into which images and text, such as images obtained from image database 920 and text obtained from prognostic description table 1200, ameliorative description table 1204, and combined description table 1208 may be inserted. Tables in narrative description table 1016 may be populated, as a non-limiting example, using submissions from experts, which may be collected according to any processes described above. Persons skilled in the art, upon reviewing the entirety of this disclosure, will be aware of various way sin which entries in narrative description table 1016 may be categorized and/or organized.

Figure 13:
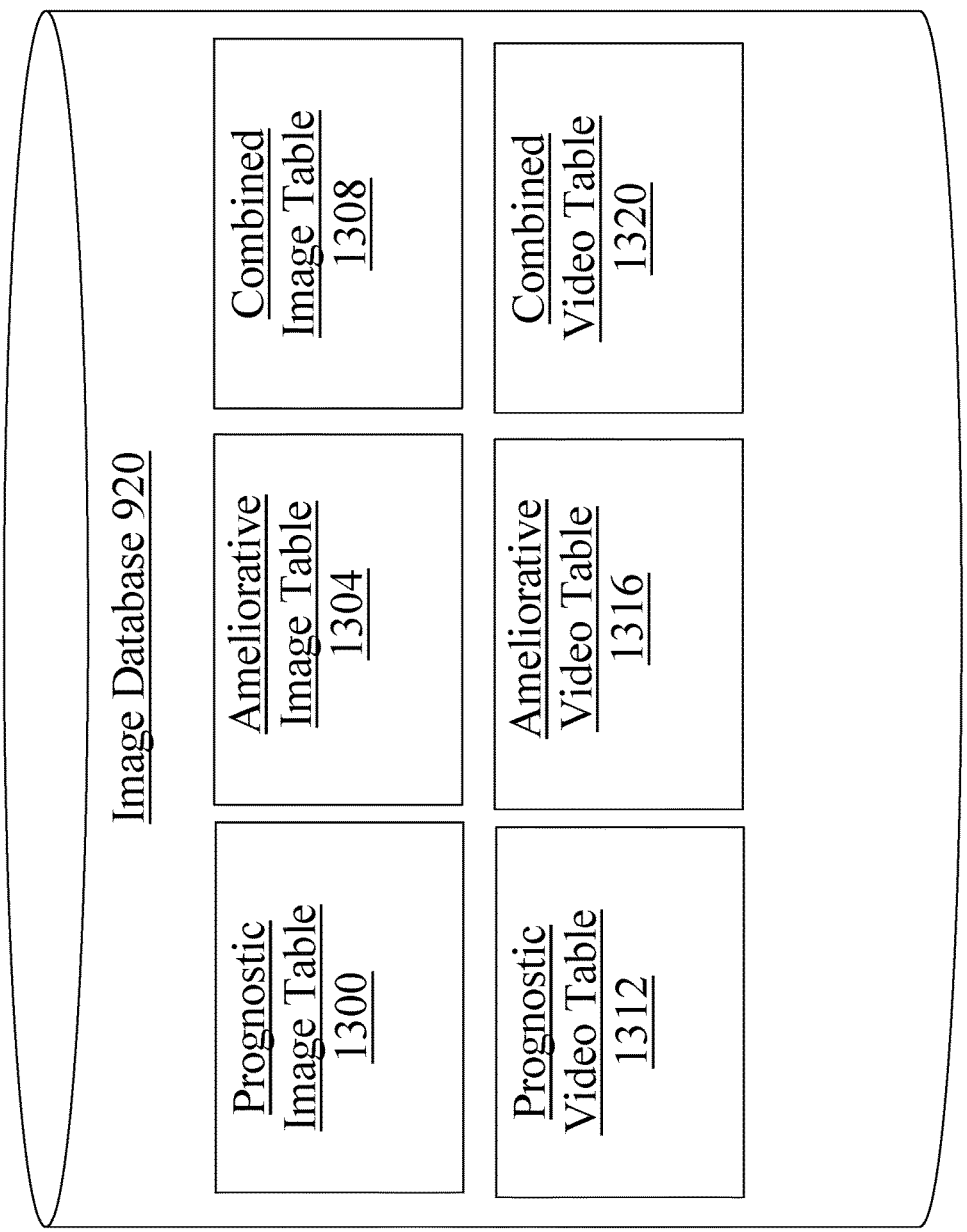
FIG. 13 is a block diagram illustrating an exemplary embodiment of an image database.

Referring now to FIG. 13, an exemplary embodiment of an image database 920 is illustrated. Image database 920 may be implemented as any database and/or datastore suitable for use as biological extraction database 300 as described above. One or more database tables in image database 102 may include, without limitation, a prognostic image table 1300, which may link prognostic labels to images associated with prognostic labels. One or more database tables in image database 920 may include, without limitation, an ameliorative image table 1304, which may link ameliorative process labels to images associated with ameliorative process labels. One or more database tables in image database 920 may include, without limitation, a combined description table 1408, which may link combinations of prognostic labels and ameliorative labels to images associated with the combinations. One or more database tables in image database 102 may include, without limitation, a prognostic video table 1312, which may link prognostic labels to videos associated with prognostic labels. One or more database tables in image database 920 may include, without limitation, an ameliorative video table 1316, which may link ameliorative process labels to videos associated with ameliorative process labels. One or more database tables in image database 920 may include, without limitation, a combined video table 1320, which may link combinations of prognostic labels and ameliorative labels to videos associated with the combinations. Tables in image database 920 may be populated, without limitation, by submissions by experts, which may be provided according to any process or process steps described in this disclosure for collection of expert submissions.

Referring again to FIG. 9, plan generator module 168 may be configured to receive at least an element of user data and filter diagnostic output using the at least an element of user data. At least an element of user data, as used herein, is any element of data describing the user, user needs, and/or user preferences. At least an element of user data may include a constitutional restriction. At least a constitutional restriction may include any health-based reason that a user may be unable to engage in a given ameliorative process; at least a constitutional restriction may include any counter-indication as described above, including an injury, a diagnosis of something preventing use of one or more ameliorative processes, an allergy or food-sensitivity issue, a medication that is counter-indicated, or the like. At least an element of user data may include at least a user preference. At least a user preference may include, without limitation, any preference to engage in or eschew any ameliorative process and/or other potential elements of a comprehensive instruction set 172, including religious preferences such as forbidden foods, medical interventions, exercise routines, or the like.

Figure 14:
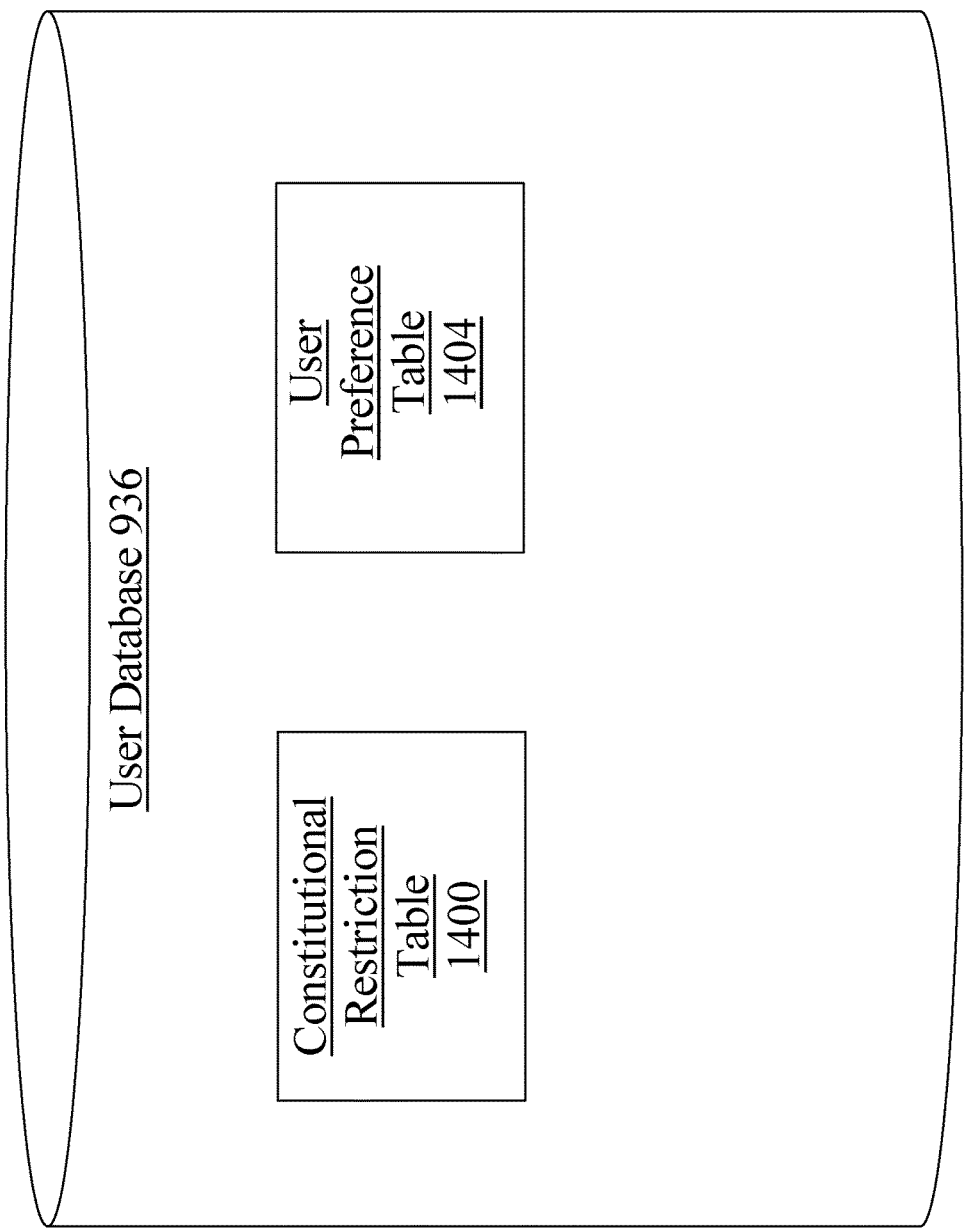
FIG. 14 is a block diagram illustrating an exemplary embodiment of a user database.

Referring to FIG. 14, an exemplary embodiment of a user database 936 is illustrated. User database 936 may be implemented as any database and/or datastore suitable for use as biological extraction database 300 as described above. One or more database tables in user database 936 may include, without limitation, a constitution restriction table 1500; at least a constitutional restriction may be linked to a given user and/or user identifier in a constitutional restriction table 1400. One or more database tables in user database 936 may include, without limitation, a user preference table 1404; at least a user preference may be linked to a given user and/or user identifier in a user preference table 1404.

Referring again to FIG. 1, system 100 may include a client-interface module 176. Client-interface module 176 may include any suitable hardware or software module. Client-interface module 176 may designed and configured to transmit comprehensive instruction set 172 to at least a user client device 180 associated with the user. A user client device 180 may include, without limitation, a display in communication with diagnostic engine 108; display may include any display as described below in reference to FIG. 19. A user client device 180 may include an addition computing device, such as a mobile device, laptop, desktop computer, or the like; as a non-limiting example, the user client device 180 may be a computer and/or workstation operated by a medical professional. Output may be displayed on at least a user client device 180 using an output graphical user interface; output graphical user interface may display at least a current prognostic descriptor 900, at least a future prognostic descriptor 924, and/or at least an ameliorative process descriptor 928.

With continued reference to FIG. 1, system 100 includes at least an advisory module executing on the at least a server 104. At least an advisory module 184 may include any suitable hardware or software module. In an embodiment, at least an advisory module 184 is designed and configured to generate at least an advisory output as a function of the comprehensive instruction set 172 and may transmit the advisory output to at least an advisor client device 188. At least an advisor client device 188 may include any device suitable for use as a user client device 180 as described above. At least an advisor client device 188 may operate on system 100 and may be a user client device 180 as described above; that is, at least an advisory output may be output to the user client device 180. Alternatively or additionally, at least an advisor client device 188 may be operated by an informed advisor, defined for the purposes of this disclosure as any person besides the user who has access to information useable to aid user in interaction with artificial intelligence advisory system. An informed advisor may include, without limitation, a medical professional such as a doctor, nurse, nurse practitioner, functional medicine practitioner, any professional with a career in medicine, nutrition, genetics, fitness, life sciences, insurance, and/or any other applicable industry that may contribute information and data to system 100 regarding medical needs. An informed advisor may include a spiritual or philosophical advisor, such as a religious leader, pastor, imam, rabbi, or the like. An informed advisor may include a physical fitness advisor, such as without limitation a personal trainer, instructor in yoga or martial arts, sports coach, or the like.

Figure 15:
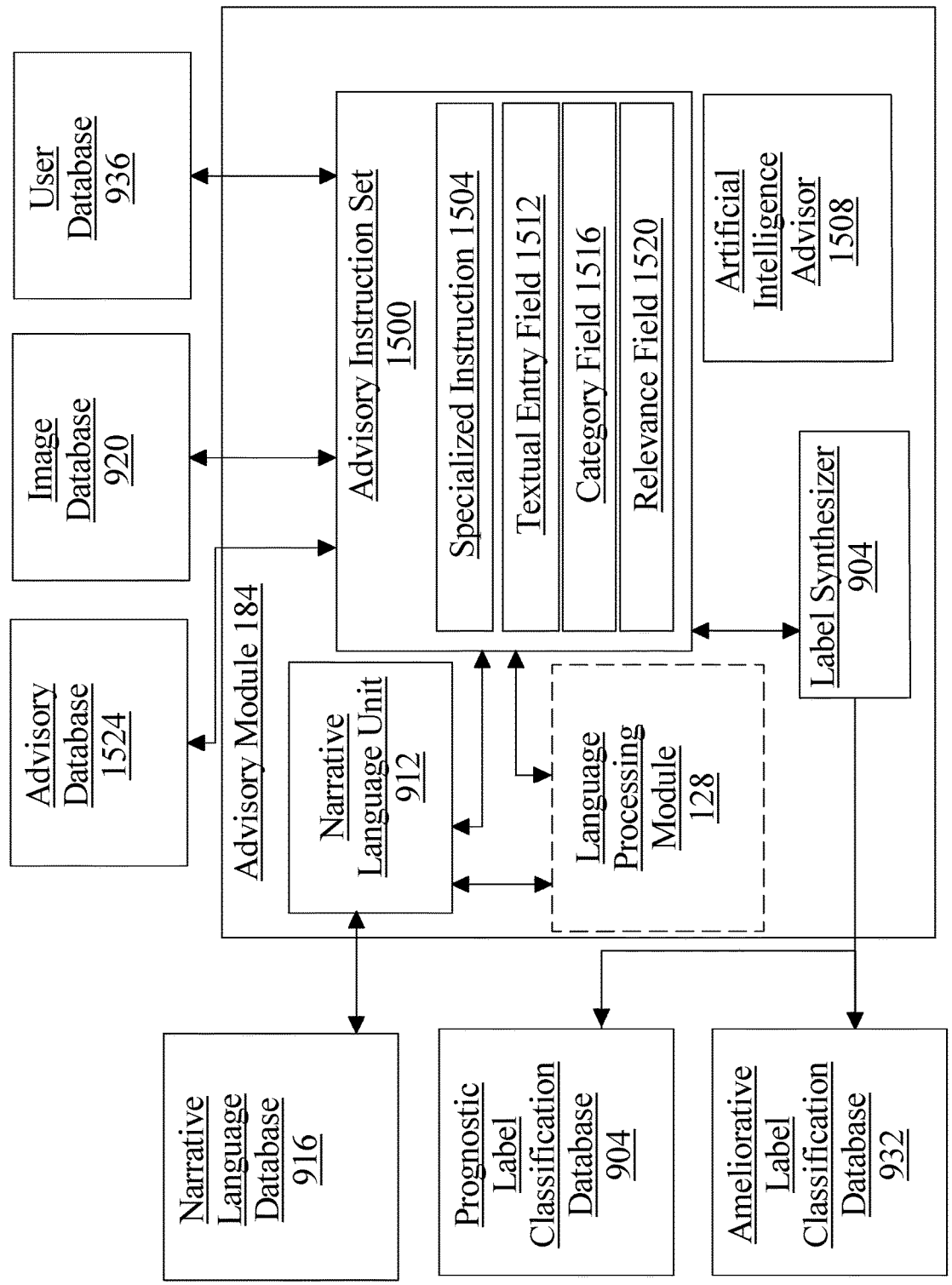
FIG. 15 is a block diagram illustrating an exemplary embodiment of an advisory module and associated system elements.

Referring now to FIG. 15, an exemplary embodiment of an advisory module 184 is illustrated. Advisory module 184 may be configured to generate an advisor instruction set 1600 as a function of the diagnostic output. Advisory instruction set 1500 may contain any element suitable for inclusion in comprehensive instruction set 172; advisory instruction set 1500 and/or any element thereof may be generated using any process suitable for generation of comprehensive instruction set 172. Advisory instruction set 1500 may include one or more specialized instructions 1504; specialized instructions, as used herein, are instructions the contents of which are selected for display to a particular informed advisor. Selection of instructions for a particular informed advisor may be obtained, without limitation, from information concerning the particular informed advisor, which may be retrieved from a user database 936 or the like. As a non-limiting example, where an informed advisor is a doctor, specialized instruction 1504 may include data from biological extraction as described above; specialized instruction may include one or more medical records of user, which may, as a non-limiting example, be downloaded or otherwise received from an external database containing medical records and/or a database (not shown) operating on at least a server 104. As a further non-limiting example medical data relevant to fitness, such as orthopedic reports, may be provided to an informed advisor whose role is as a fitness instructor, coach, or the like.

In an embodiment, and continuing to refer to FIG. 15, advisory module 184 may be configured to receive at least an advisory input from the advisor client device 188. At least an advisory input may include any information provided by an informed advisor via advisor client device 188. Advisory input may include medical information and/or advice. Advisory input may include user data, including user habits, preferences, religious affiliations, constitutional restrictions, or the like. Advisory input may include spiritual and/or religious advice. Advisory input may include user-specific diagnostic information. Advisory input may be provided to user client device 180; alternatively or additionally, advisory input may be fed back into system 100, including without limitation insertion into user database 936, inclusion in or use to update diagnostic engine 108, for instance by augmenting machine-learning models and/or modifying machine-learning outputs via a lazy-learning protocol or the like as described above.

With continued reference to FIG. 15, advisory module 184 may include an artificial intelligence advisor 1508 configured to perform a user textual conversation with the user client device 180. Artificial intelligence advisor 1508 may provide output to advisor client device 188 and/or user client device 180. Artificial intelligence advisor 1508 may receive inputs from advisor client device 188 and/or user client device 180. Inputs and/or outputs may be exchanged using messaging services and/or protocols, including without limitation any instant messaging protocols. Persons skilled in the art, up reviewing the entirety of this disclosure, will be aware of a multiplicity of communication protocols that may be employed to exchange text messages as described herein. Text messages may be provided in textual form and/or as audio files using, without limitation, speech-to-text and/or text-to-speech algorithms.

With continued reference to FIG. 15, advisory module 184 may output, with advisory output, a textual entry field 1512. Textual entry field 1512 may include a searchable input field that allows entry of a search term such as a word or phrase to be entered by a user such as an informed advisor. In an embodiment, textual entry field 1512 may allow for entry of a search term to be matched with labels contained within the at least at diagnostic output. For example, an informed advisor such as a medical professional may enter into a search term a results of a fasting glucose test after receiving at least a diagnostic output of diabetes. In such an instance, user such as an informed advisor may be able to search multiple results such as fasting glucose test levels recorded over a certain period of time such as several years and/or months. In yet another non-limiting example, an informed advisor such as a fitness professional may search for user's most recent exercise log and/or nutrition records. In yet another non-limiting example, an informed advisor such as a nurse practitioner may enter information into textual entry field 1512 to search for information pertaining to user's medication history after receiving at least a diagnostic output of acute kidney injury. In an embodiment, textual entry field 1512 may allow a user such as an informed advisor to navigate different areas of advisory output. For example, an informed advisor may utilize textual entry field 1512 to navigate to different locations such as a table of contents, and or sections organized into different categories as described in more detail below.

With continued reference to FIG. 15, advisory module 184 may include in an advisory output a category field 1516. Category field 1516 may include a textual field that contains advisory output organized into categories. Category, as used herein, is any breakdown of advisory output by shared characteristics. Categories may include for example, breakdown by informed advisor type. For example, informed advisors may be categorized into categories of expertise such as spiritual professionals, nutrition professionals, fitness professionals and the like. Categories may include sub-categories of specialties such as for example functional medicine informed advisors may be organized into sub-categories based on body system they may be treating. This could include sub-categories such as dermatology specialists, Genito-urology specialists, gastroenterology specialists, neurology specialists and the like. Categories may include a breakdown by time such as chronological order and/or reverse chronological order. Categories may be modified and/or organized into test results such as for example all complete blood counts that a user has ever had performed may be located in one category, and all CT scans that a user has had performed may be located in another category. Categories may include a breakdown by relevance, such as highly relevant test results and/or test results that are outside normal limits.

With continued reference to FIG. 15, advisory module 184 may include in an advisory output a relevance field 1520. Relevance field 1520 as used herein is a textual field that contains advisory output information labeled as being relevant. Relevance, as used herein, is any information contained within advisory output that is closely connected and/or related to diagnostic output. Relevance may include information that would be of interest to a particular category of informed advisor. For example, an informed advisor such as an ophthalmologist may deem information contained within at least an advisory output such as a measurement of a user's intra-ocular pressure to be of relevance, while an advisory output containing information summarizing a user's last appointment with a podiatrist to not be of relevance. In yet another non-limiting example, an informed advisor such as a fitness professional may deem information contained within an advisory output such as a summary of a user's last appointment with an orthopedic doctor to be relevant while a summary of a user's last colonoscopy may not be relevant. In an embodiment, relevance may be viewed on a continuum. Information contained within at least an advisory output that directly relates to an informed advisor and is of high probative value to an informed advisor may be highly relevant. For example, a nutritionist may deem a journal of a user's eating habits as highly relevant. In yet another non-limiting example, a spiritual professional may deem a summary of a user's church patterns as highly relevant. Information that is related to an informed advisor but does not directly affect an informed advisor may be moderately relevant. For example, a dermatologist may deem information pertaining to a user's last physical exam with an internal medicine doctor to be moderately relevant. In yet another non-limiting example, an endocrinologist may deem information pertaining to a user's last appointment with a podiatrist to be moderately relevant for a user diagnosed with diabetes. Information that is not related to an informed advisor and does not affect an informed advisor may be of low relevance. For example, a trauma surgeon may deem information about a user's last dental cleaning to be of low relevance. In yet another non-limiting example, a cardiologist may deem information about a user's last bone density scan to be of low relevance. In an embodiment, user such as informed advisor may use textual entry field 1512 to navigate advisory output to find information that is relevant. In an embodiment, information contained within at least an advisory output may be marked as relevant such as by another informed advisor. For example, a functional medicine doctor may mark an elevated fasting blood glucose level as relevant before transmitting such a result to a nutrition professional.

In an embodiment, and still referring to FIG. 15, a relevance field 1520 may include an image, link, or other visual element that an informed advisor may select or otherwise interact with to expand or contract a portion of advisory output; for instance, relevance field 1520 may include a symbol next to or on a section heading that can cause a corresponding section of text to display when activated a first time and disappear when activated a second time. As a result, an informed advisor may be presented initially with some text visible and other text not visible; initial presentation may hide all text but section headers. Alternatively or additionally, where informed advisor belongs to a particular category of informed advisor and/or has a profile in, for instance, advisory database 1524 indicating categories of interest to the informed advisor, sections of text and/or images related to such categories may initially display while other sections do not display unless a relevance field 1520 corresponding to such sections is selected by the informed advisor.

With continued reference to FIG. 15, advisory module 184 contains advisory database 1524. Advisory database 1524 may be implemented as any database and/or datastore suitable for use as an advisory database. An exemplary embodiment of an advisory database 1524 is provided below in FIG. 17.

Figure 16:
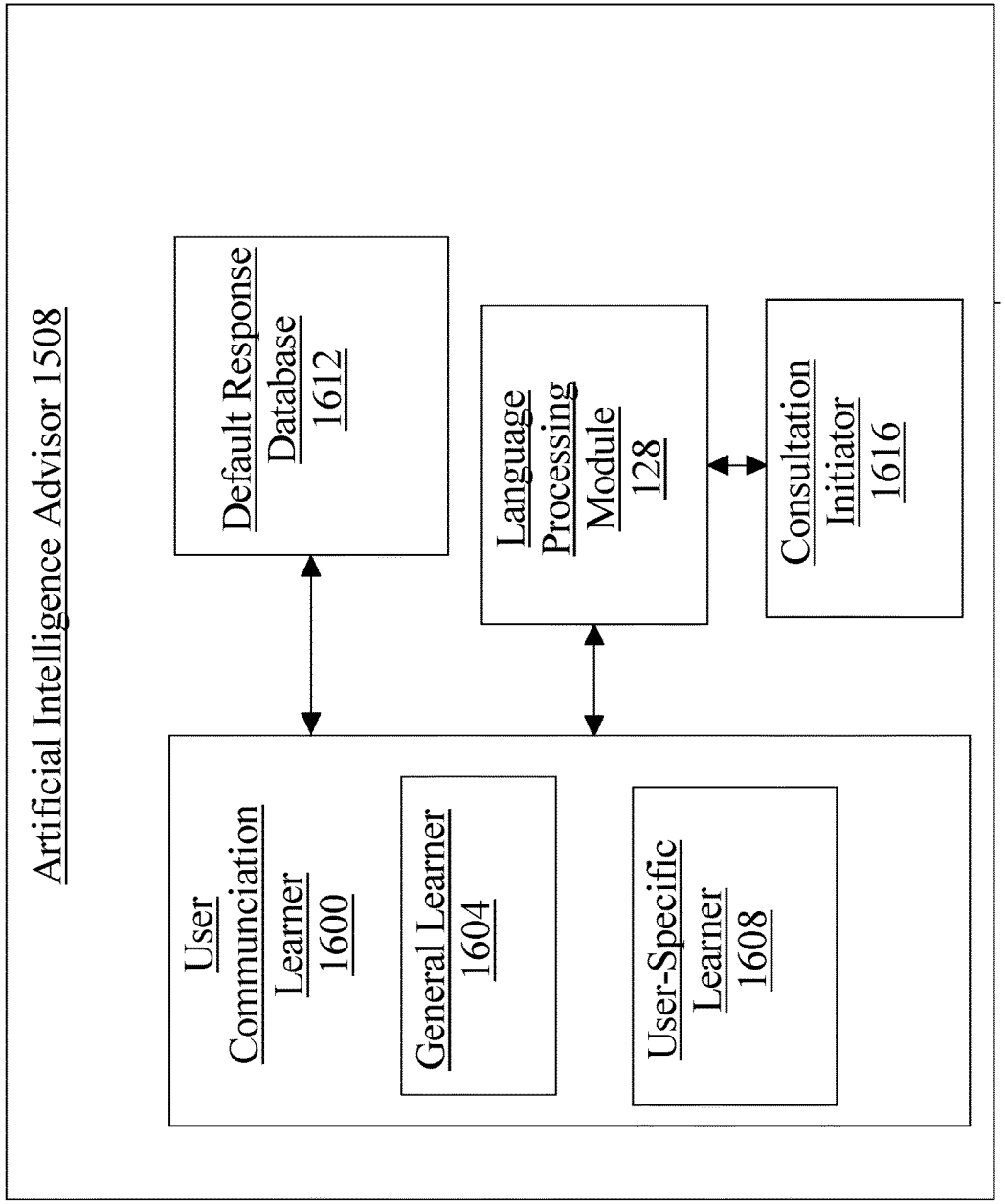
FIG. 16 is a block diagram illustrating an exemplary embodiment of an artificial intelligence advisor and associated system elements.

Referring now to FIG. 16, an exemplary embodiment of an artificial intelligence advisor 1508 is illustrated. Artificial intelligence advisor 1508 may include a user communication learner 1600. User communication learner 1600 may be any form of machine-learning learner as described above, implementing any form of language processing and/or machine learning. In an embodiment, user communication learner 1600 may include a general learner 1604; general learner 1604 may be a learner that derives relationships between user inputs and correct outputs using a training set that includes, without limitation, a corpus of previous conversations. Corpus of previous conversations may be logged by at least a server 104 as conversations take place; user feedback, and/or one or more functions indicating degree of success of a conversation may be used to differentiate between positive input-output pairs to use for training and negative input-output pairs not to use for training. Outputs may include textual strings and/or outputs from any databases, modules, and/or learners as described in this disclosure, including without limitation prognostic labels, prognostic descriptors, ameliorative labels, ameliorative descriptors, user information, or the like; for instance, general learner 1604 may determine that some inputs optimally map to textual response outputs, while other inputs map to outputs created by retrieval of module and/or database outputs, such as retrieval of prognostic descriptors, ameliorative descriptors, or the like. User communication learner may include a user-specific learner 1608, which may generate one or more modules that learn input-output pairs pertaining to communication with a particular user; a user specific learner 1708 may initially use input-output pairs established by general learner 1604 and may modify such pairs to match optimal conversation with the particular user by iteratively minimizing an error function.

Still referring to FIG. 16, general learner 1604 and/or user-specific learner 1608 may initialize, prior to training, using one or more record retrieved from a default response database 1612. Default response database 1612 may link inputs to outputs according to initial relationships entered by users, including without limitation experts as described above, and/or as created by a previous instance or version of general learner 1604 and/or user-specific learner 1608. Default response database 1612 may periodically be updated with information from newly generated instances of general learner 1604 and/or user-specific learner 1608. Inputs received by artificial intelligence advisor 1508 may be mapped to canonical and/or representative inputs by synonym detection as performed, for instance, by a language processing module 128; language processing module 128 may be involved in textual analysis and/or generation of text at any other point in machine-learning and/or communication processes undergone by artificial intelligence advisor 1508.

Figure 17:
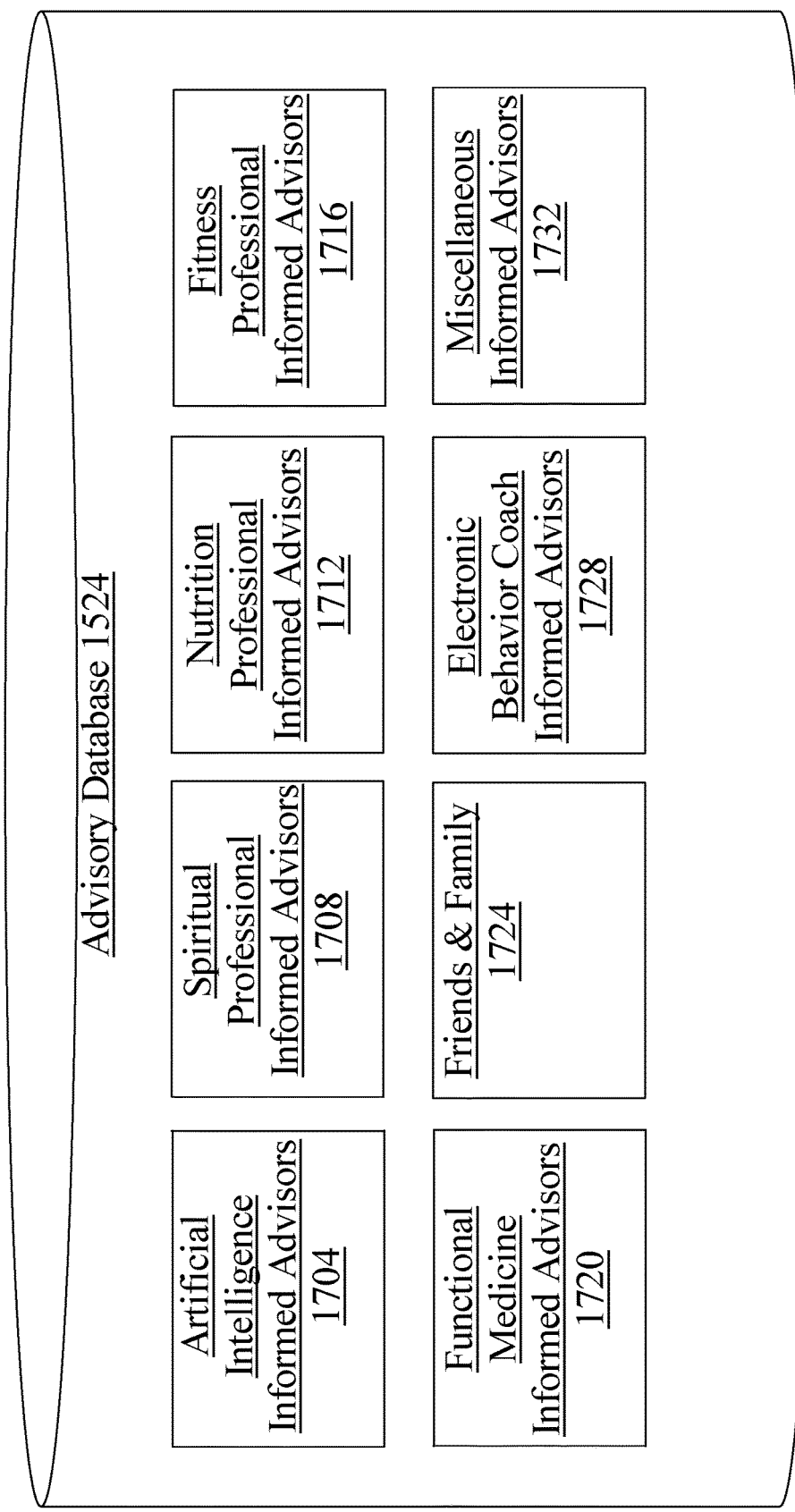
FIG. 17 is a block diagram illustrating an exemplary embodiment of an advisory database.

Referring now to FIG. 17, an exemplary embodiment of advisory database 1524 is illustrated. One or more database tables in advisory database 1524 may link to data surrounding an informed advisor. Advisory database 1524 may include one or more database tables categorized by expertise of informed advisor. One or more database tables in advisory database 1524 may include, without limitation, an artificial intelligence informed advisors table 1704, which may contain any and all information pertaining to artificial intelligence informed advisors. One or more database tables in advisory database 1524 may include, without limitation, a spiritual professional informed advisors table 1708, which may contain any and all information pertaining to spiritual professional informed advisors. Spiritual professional informed advisors may include spiritual professionals who may participate in cultivating spirituality through exercise of practices such as prayer, meditation, breath work, energy work, and the like. One or more database tables in advisory database 1524 may include, without limitation, a nutrition professional informed advisors table 1712, which may include any and all information pertaining to nutritional informed advisors. Nutritional informed advisors may include dieticians, chefs, and nutritionists who may offer expertise around a user's diet and nutrition state and supplementation. One or more database tables in advisory database 1524 may include, without limitation a fitness professional informed advisors table 1716, which may include any and all information pertaining to fitness professional informed advisors. Fitness professional informed advisors may examine the fitness state of a user and may include personal trainers, coaches, group exercise instructors, and the like. One or more database tables in advisory database 1524 may include, without limitation a functional medicine informed advisors table 1720, which may include any and all information pertaining to functional medicine informed advisors. Functional medicine informed advisors may include doctors, nurses, physician assistants, nurse practitioners and other members of the health care team. One or more database tables in advisory database 1524 may include, without limitation a friends and family informed advisors table 1724, which may include any and all information pertaining to friends and family informed advisors. Friends and family informed advisors may include friends and family members of a user who may create a positive community of support for a user. One or more database tables in advisory database 1524 may include, without limitation an electronic behavior coach informed advisor table 1728, which may include any and all information pertaining to electronic behavior coach informed advisors. Electronic behavior coach informed advisors may assist a user in achieving certain results such as modifying behaviors to achieve a result such as assisting in addition recovery and/or changing a user's eating habits to lose weight. One or more database tables in advisory database 1524 may include without limitation a miscellaneous informed advisor table 1732, which may include any and all information pertaining to miscellaneous informed advisors. Miscellaneous informed advisors may include any informed advisors who do not fit into one of the categories such as for example insurance coverage informed advisors. Miscellaneous informed advisor table 1732 may also contain miscellaneous information pertaining to informed advisors such as a user's preference for informed advisors in a certain geographical location and/or other preferences for informed advisors.

Figure 18:
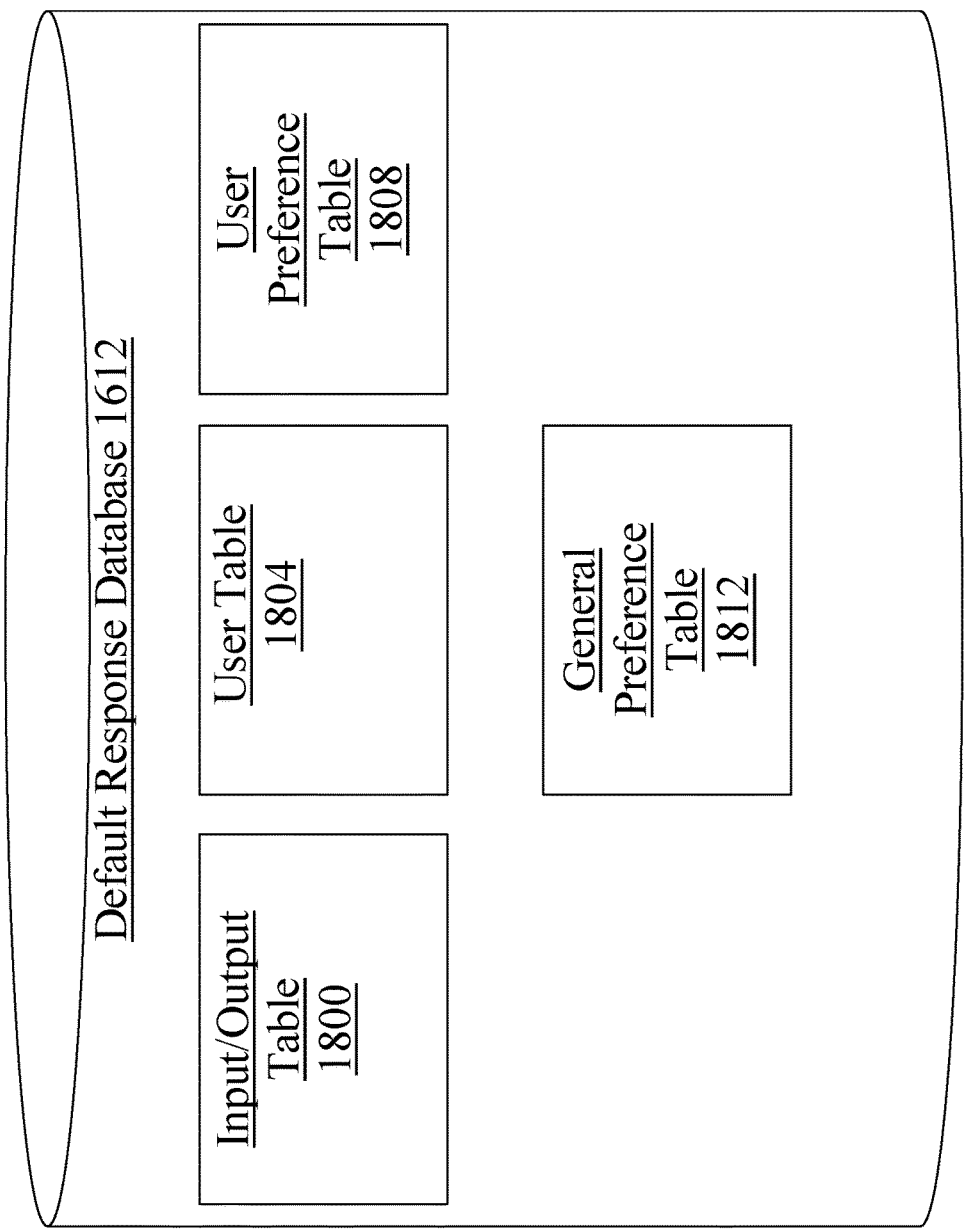
FIG. 18 is a block diagram illustrating an exemplary embodiment of a default response database.

Referring now to FIG. 18, an exemplary embodiment of a default response database 1612 is illustrated. Default response database 1612 may be implemented as any database and/or datastore suitable for use as biological extraction database 300 as described above. One or more database tables in default response database 1612 may include, without limitation, an input/output table 1800, which may link default inputs to default outputs. Default response database 1612 may include a user table 1804, which may, for instance, map users and/or a user client device 180 to particular user-specific learners and/or past conversations. Default response database 1612 may include a user preference table 1808 listing preferred modes of address, turns of phrase, or other user-specific communication preferences. Default response database 1612 may include a general preference table 1812, which may track, for instance, output-input pairings associated with greater degrees of user satisfaction.

Referring again to FIG. 16, artificial intelligence advisor may include a consultation initiator 1616 configured to detect a consultation event in a user textual conversation and initiate a consultation with an informed advisor as a function of the consultation event. A consultation event, as used herein, is a situation where an informed advisor is needed to address a user's situation or concerns, such as when a user should be consulting with a doctor regarding an apparent medical emergency or new condition, or with an advisor who can lend emotional support when particularly distraught. Detection may be performed, without limitation, by matching an input and/or set of inputs to an output that constitutes an action of initiating a consultation; such a pairing of an input and/or input set may be learned using a machine learning process, for instance via general learner and/or user specific learner 1608. In the latter case, information concerning a particular user's physical or emotional needs or condition may be a part of the training set used to generate the input/input set to consultation event pairing; for instance, a user with a history of heart disease may trigger consultation events upon any inputs describing shortness of breath, chest discomfort, arrhythmia, or the like. Initiation of consultation may include transmitting a message to an advisor client device 188 associated with an appropriate informed advisor, such as without limitation transmission of information regarding a potential medical emergency to a doctor able to assist in treating the emergency. Initiation of consultation may alternatively or additionally include providing an output to the user informing the user that a consultation with an informed advisor, who may be specified by name or role, is advisable.

Figure 19:
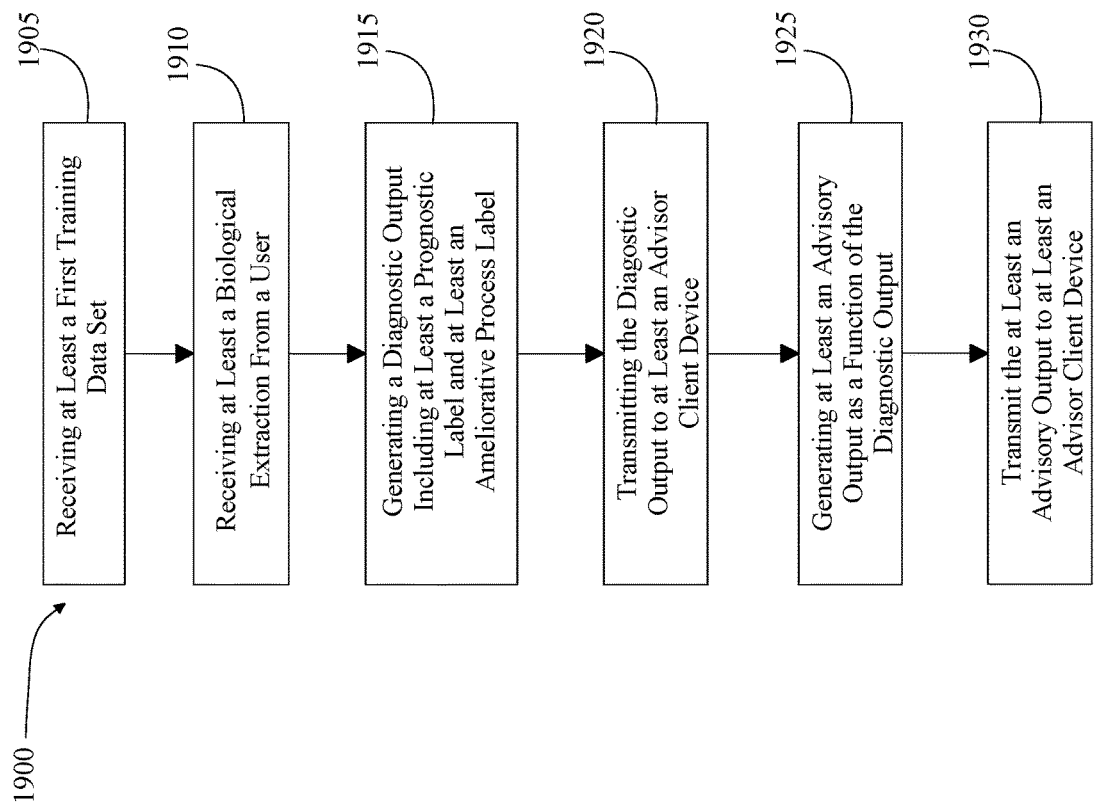
FIG. 19 is a flow diagram illustrating an exemplary embodiment of a method of utilizing diagnostics for informed vibrant constitutional guidance.

Referring now to FIG. 19, an exemplary embodiment of a method 1900 of utilizing diagnostics for informed vibrant constitutional guidance is illustrated. At step 1905, a diagnostic engine 108 receives training data. Training data includes a first training set 112 including a plurality of first data entries, each first data entry of the first training set 112 including at least an element of physiological state data 116 and at least a correlated prognostic label. In an embodiment, receiving the first training set 112 may include associating the at least an element of physiological state data 116 with at least a category from a list of significant categories of physiological state data 116. Receiving the list of significant categories from at least an expert. Receiving the first training set 112 may include associating the at least correlated first prognostic label 120 with at least a category from a list of significant categories of prognostic labels.

With continued reference to FIG. 19, training data includes a second training set 132 including a plurality of second data entries, each second data entry of the first training set 112 including at least a prognostic label and at least a correlated ameliorative process label 140. In an embodiment, receiving second training set 132 may include associating at least second prognostic label 136 with at least a category from a list of significant categories of prognostic labels. Receiving second training set 132 may include associating at least correlated ameliorative process label 140 with at least a category from a list of significant categories of ameliorative process labels 140.

With continued reference to FIG. 19, receiving the second training set 132 further comprises receiving at least a document describing at least a medical history and extracting at least a second data entry of the plurality of second data entries from the at least a document.

With continued reference to FIG. 19, receiving the second training set 132 further comprises receiving from at least an expect, at least a second data entry of the plurality of second data entries.

With continued reference to FIG. 19, at step 1910 diagnostic engine 108 operating on the at least a server 104 receives at least a biological extraction from a user. Receiving at least a biological extraction from a user may include receiving at a physically extracted sample. This may include for example, receiving a blood sample of a user, an endocrinal sample, a DNA sample, an RNA sample and the like. Receiving at least a biological extraction may be implemented, without limitation, as described above in reference to FIGS. 1-18.

With continued reference to FIG. 19, at step 1915 diagnostic engine 108 operating on the at least a server 104 generates a diagnostic output based on the at least a biological extraction. Diagnostic output includes at least a prognostic label and at least an ameliorative process label. Prognostic label may be generated by prognostic label learner 152 operating on diagnostic engine 108. Prognostic label may be generated as a function of the first training set and at least a biological extraction. Prognostic output may be generated by a lazy learning as a function of the first training set and the at least a biological extraction.

Prognostic label may be generated by at least a first machine-learning model 156 relating physiological state data to prognostic labels. For example, one or more models may determine relationships between physiological state data and prognostic labels. Relationships may include linear regression models and may be modeled around relationships between physiological state data and current prognostic labels. Prognostic output may be generated as a function of a classification of the prognostic label. Prognostic labels may be categorized into different pairings and/or groupings as described above in reference to FIGS. 1-18. Machine-learning may examine relationships between physiological state data and prognostic labels. Machine-learning algorithms may include any and all algorithms as performed by any modules as described in this disclosure, including without limitation algorithms described above regarding prognostic label learner 152 and/or language processing module 128. For example, machine-learning may examine relationships between 25-hydroxy Vitamin D levels and current diagnosis of seasonal affective disorder (SAD). Machine-learning may examine relationships between physiological state data such as a precursor condition and subsequent development of a condition, such as blood tests that are positive for varicella zoster virus (chicken pox) and subsequent diagnosis of herpes zoster, commonly known as shingles. Machine-learning models may examine relationships between current population of an individual's internal microbiome such as presence of commensal *Clostridioides Difficile* (*C. difficile*) and later development and diagnosis of pathogenic *C. difficile* infection. Machine-learning models may examine relationships between current population of an individual's external microbiome such as presence of commensal *Staphylococcus Aureus* species and later development and diagnosis of pathogenic infections such as Methicillin-Resistant *Staphylococcus aureus* (MRSA). Machine-learning models may examine relationships between current physiological state and future development and diagnosis of a disease or condition such as the presence of Breast Cancer Gene 1 (BRCA1) and/or Breast Cancer Gene 2 (BRCA2) and later development and diagnosis of breast cancer and/or other cancers such as stomach cancer, pancreatic cancer, prostate cancer, and/or colon cancer. Machine-learning models may examine relationships between physiological state data and diagnosed conditions such as triglyceride level, fasting glucose level, HDL cholesterol level, waist circumference, and/or systolic blood pressure and later development and diagnosis of metabolic syndrome. Machine-learning models may examine precursor state and rate of progression to diagnosis, such as appearance of drusen underneath the retina and/or angiography and rate of progression to diagnosis of macular degeneration. Machine-learning models may examine age of user at precursor state and rate of progression to diagnosis, such as appearance of drusen in a 20-year-old and subsequent age of diagnosis of macular degeneration as compared to appearance of drusen in an 85-year-old and subsequent age of diagnosis of macular degeneration. Machine-learning models may examine relationships between a plurality of prognostic labels and root cause analysis, such as for example, prognostic labels that include presence of joint pain, limited mobility, elevated fasting glucose levels, and high body mass index (BMI) may indicate possible linkages to a root cause prognostic label of obesity. In yet another non-limiting example, a plurality of prognostic labels such as presence of *Acanthosis nigricans*, elevated fasting blood sugar (blood glucose level greater than 100 mg/dL), endometrial hyperplasia, elevated blood pressure (greater than 130 mmHg systolic and/or greater than 80 mmHg diastolic), elevated total cholesterol levels (greater than 200 mg/dL), and elevated triglycerides (greater than 200 mg/dL) may indicate possible linkages to a root cause prognostic label of Polycystic Ovarian Syndrome (PCOS). Machine-learning models may examine correlations and relationships between physiological state and overall mortality such as for example measurement of telomeric DNA length and mortality. In yet another non-limiting example, machine-learning models may examine telomeric DNA length and subsequent diagnosis of diseases such as cardiovascular disease, diabetes, leukemia and the like. Machine-learning models may examine correlations and relationships between physiological state and severity and/or how rapidly a disease progresses such as pancreatic cancer. Machine-learning models may examine factors such as age of onset and how rapidly a disease progresses such as neurological diseases including for example Alzheimer's disease, Parkinson's disease, Bell's palsy, Lupus, stroke, rheumatoid arthritis, multiple sclerosis and the like. Prognostic label learner 152 may generate prognostic output from prognostic label as a function of the first training data set and at least a biological extraction. This may be done by any of the methodologies as described above. Prognostic output may be generated as a function of a classification of prognostic label. This may be done by any of the methodologies as described above.

With continued reference to FIG. 19, diagnostic engine 108 generates at least a diagnostic output include at least an ameliorative process label. Ameliorative process label may be generated by ameliorative label learner 140 operating on diagnostic engine 108. Ameliorative process label may be generated as a function of the second training set and at least a prognostic output. Ameliorative process label may be generated by a lazy learning as a function of the second training set and at least an ameliorative process descriptor.

With continued reference to FIG. 19, ameliorative process label learner generates the at least an ameliorative output by creating a second-machine learning model using the second training set relating prognostic labels to ameliorative labels. Second machine-learning model may use ameliorative label to generate at least an ameliorative output. Ameliorative output may be generated as a function of a classification of the at least a prognostic output. Prognostic output may be classified by any schematic as described above in reference to FIGS. 1-18. Second machine learning-model may use models to create correlations relating a prognostic output such as osteoarthritis to an ameliorative label with an exercise recommendation that includes walking, swimming and/or biking so as to be easy on the joints. In yet another example, machine-learning models may create correlations relating a prognostic output such as coronary artery occlusion to an ameliorative label such as angioplasty. Machine-learning models may group certain prognostic outputs to generate ameliorative labels. For example, prognostic outputs that include disease states associated with impaired fasting blood sugar such as diabetes, polycystic ovarian syndrome, cardiovascular disease, metabolic syndrome, and the like may be linked to an ameliorative label that includes an aerobic exercise regimen. In yet another non-limiting example, prognostic outputs that indicate a risk factor for cardiovascular disease such as uncontrolled hypertension, physical inactivity, obesity, uncontrolled diabetes, congenital heart disease, family history of heart disease, positive smoking status, high cholesterol, high triglycerides, low HDL, and the like may be linked to an ameliorative label that includes a recommendation to check 25-hydroxy vitamin D blood test. In yet another non-limiting example, machine-learning models may be utilized so that a prognostic output that is indicative of early aging such as short telomer length may be linked to an ameliorative label that includes anti-aging supplementation such as bioidentical hormone replacement therapy, pregnenolone supplementation, resveratrol supplementation, coenzyme q10 supplementation and the like. Machine-learning models may be utilized so that an ameliorative label may be linked to a prognostic output that includes a future risk of developing a disease or condition. For example, a prognostic output that includes a positive BRCA1 diagnosis may be associated with an ameliorative label that includes dietary recommendations containing high consumption of cruciferous vegetables. In yet another non-limiting example, a prognostic output that includes a positive presence of commensal *C. difficile* may be associated with an ameliorative label that includes recommendations to supplement with *Saccharomyces Boulardii*. Ameliorative output may be generated as a function of the second training data set and the at least a prognostic output. This may be performed by any of the methodologies as described above. Ameliorative output may be generated a function of a classification of the at least a prognostic output. This may be performed by any of the methodologies as described above.

With continued reference to FIG. 19, at step 1920 diagnostic engine 108 transmits the diagnostic output including at least a prognostic output and at least an ameliorative output to at least an advisor client device. Transmission may be implemented for example, as described above in reference to FIG. 1.

With continued reference to FIG. 19, at step 1925 at least an advisory module 184 operating on the at least a server 104 generates at least an advisory output as a function of the diagnostic output. Advisory module 184 may receive at least an informed advisor input. Generating at least an advisory output as a function of the diagnostic output may include evaluating at least an informed advisor input. Language processing module 128 may evaluate at least an informed advisor input and extract one or more words. In an embodiment, diagnostic engine 108 may transmit at least an output to an advisor client device. Informed advisor such as a functional medicine doctor may evaluate the at least an output and may provide feedback. Feedback could include evaluation of diagnostic output generated by diagnostic engine 108. For example, diagnostic engine 108 may generate an output that contains 3 possible diagnoses including chicken pox, contact dermatitis, and an immunoglobulin E (IgE) mediated maculopapular rash to a food allergen, for a user complaining of an itchy red rash. Upon receiving diagnostic output from diagnostic engine 108 at advisor client device 132, functional medicine doctor may have an in-person and/or electronic meeting with user whereby functional medicine doctor can perform a physical examination and view user's rash. Functional medicine doctor may be able to eliminate possible diagnoses using functional medicine doctor's medical knowledge and experience, and upon viewing using, and may generate at least an advisory input indicating such input. In such an instance, language processing module 128 may evaluate functional medicine doctor's input and may examine input for key words or phrases such as for example "diagnosis is confirmed to chicken pox" or "user is not diagnosed with contact dermatitis." Such information may then be utilized by advisory module 184 to generate at least an advisory output.

Continuing to view FIG. 19, advisory module 184 may generate advisory output containing textual elements that may allow an informed advisor to analyze advisory output based on information that is pertinent to informed advisor. Advisory output may include for example specialized instruction set 1504, textual entry field 1512, category field 1516, and/or relevance field 1520 as described in more detail above in reference to FIG. 15. Any of the textual fields as listed above may be generated to allow an informed advisor to search and/or browse through a large quantity of data relatively quickly to find an item of interest. Textual fields may allow for example an informed advisor to browse to a table of contents to find pertinent information such as a certain test result or results from a procedure that were obtained as described in more detail above in FIG. 15. Textual fields may allow an informed advisor to have an advisory output open to most relevant results, such as a cardiologist who may be interested in relevant results such as cholesterol measurements and fasting glucose levels. Textual fields may allow an informed advisor to generate an advisory output to another informed advisor containing information of relevance. For example, a functional medicine doctor may share relevant information surrounding a user's mental health with friends and family for a user suffering with depression. This may include information such as a user's response to a medication and/or supplement to treat user's depression. Textual fields may be implemented and may include any of the textual fields as described above in reference to FIG. 15.

With continued reference to FIG. 19, at step 1930 at least an advisory module 184 operating on the at least a server 104 transmits the at least an advisory output to at least an advisor client device. Transmission may be implemented for example, as described above in reference to FIG. 1.

With continued reference to FIG. 19, a plan generator module 168 operating on the at least a server 104 may generate a comprehensive instruction set associated with a user as a function of the diagnostic output at the at least an advisory output. For instance and without limitation, generating comprehensive instruction set 172 may include determining that a first prognostic label of the at least a prognostic label and a second prognostic label of the at least a prognostic label belong to a shared category and adding a category label associated with the shared category to the comprehensive instruction set 172. As an additional example, generating the comprehensive instruction set 172 may include determining a first ameliorative label of the at least an ameliorative label is a duplicate of a second ameliorative label of the at least an ameliorative label, and eliminating the first prognostic label. As an additional example, generating comprehensive instruction set 172 may include determining that a first ameliorative label of the at least an ameliorative label and a second ameliorative label of the at least an ameliorative label belong to a shared category and adding a category label associated with the shared category to the comprehensive instruction set 172. Generating comprehensive instruction set 172 may include, as a further example, receiving at least an element of user data and filtering the diagnostic output using the at least an element of user data. Comprehensive instruction set 172 may be transmitted to user client device 180.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 20:
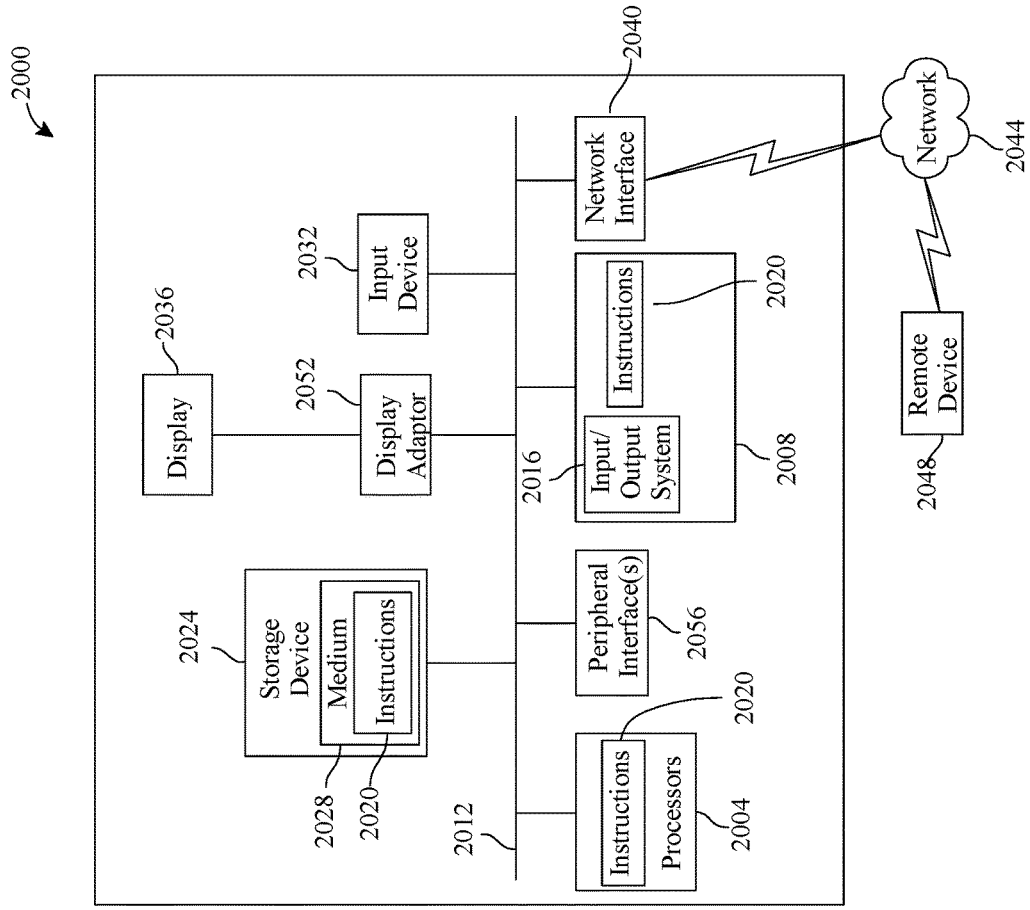
FIG. 20 is a block diagram of a computing system that can be used to implement any one or more of the methodologies disclosed herein and any one or more portions thereof.

FIG. 20 shows a diagrammatic representation of one embodiment of a computing device in the exemplary form of a computer system 2000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2000 includes a processor 2004 and a memory 2008 that communicate with each other, and with other components, via a bus 2012. Bus 2012 may include any of several types of bus structures including, but not limited to, a memory bus, a memory controller, a peripheral bus, a local bus, and any combinations thereof, using any of a variety of bus architectures.

Memory 2008 may include various components (e.g., machine-readable media) including, but not limited to, a random-access memory component, a read only component, and any combinations thereof. In one example, a basic input/output system 2016 (BIOS), including basic routines that help to transfer information between elements within computer system 2000, such as during start-up, may be stored in memory 2008. Memory 2008 may also include (e.g., stored on one or more machine-readable media) instructions (e.g., software) 2020 embodying any one or more of the aspects and/or methodologies of the present disclosure. In another example, memory 2008 may further include any number of program modules including, but not limited to, an operating system, one or more application programs, other program modules, program data, and any combinations thereof.

Computer system 2000 may also include a storage device 2024. Examples of a storage device (e.g., storage device 2024) include, but are not limited to, a hard disk drive, a magnetic disk drive, an optical disc drive in combination with an optical medium, a solid-state memory device, and any combinations thereof. Storage device 2024 may be connected to bus 2012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2024 (or one or more components thereof) may be removably interfaced with computer system 2000 (e.g., via an external port connector (not shown)). Particularly, storage device 2024 and an associated machine-readable medium 2028 may provide nonvolatile and/or volatile storage of machine-readable instructions, data structures, program modules, and/or other data for computer system 2000. In one example, software 2020 may reside, completely or partially, within machine-readable medium 2028. In another example, software 2020 may reside, completely or partially, within processor 2004.

Computer system 2000 may also include an input device 2032. In one example, a user of computer system 2000 may enter commands and/or other information into computer system 2000 via input device 2032. Examples of an input device 2032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2032 may be interfaced to bus 2012 via any of a variety of interfaces (not shown) including, but not limited to, a serial interface, a parallel interface, a game port, a USB interface, a FIREWIRE interface, a direct interface to bus 2012, and any combinations thereof. Input device 2032 may include a touch screen interface that may be a part of or separate from display 2036, discussed further below. Input device 2032 may be utilized as a user selection device for selecting one or more graphical representations in a graphical interface as described above.

A user may also input commands and/or other information to computer system 2000 via storage device 2024 (e.g., a removable disk drive, a flash drive, etc.) and/or network interface device 2040. A network interface device, such as network interface device 2040, may be utilized for connecting computer system 2000 to one or more of a variety of networks, such as network 2044, and one or more remote devices 2048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2044, may employ a wired and/or a wireless mode of communication. In general, any network topology may be used. Information (e.g., data, software 2020, etc.) may be communicated to and/or from computer system 2000 via network interface device 2040.

Computer system 2000 may further include a video display adapter 2052 for communicating a displayable image to a display device, such as display device 2036. Examples of a display device include, but are not limited to, a liquid crystal display (LCD), a cathode ray tube (CRT), a plasma display, a light emitting diode (LED) display, and any combinations thereof. Display adapter 2052 and display device 2036 may be utilized in combination with processor 2004 to provide graphical representations of aspects of the present disclosure. In addition to a display device, computer system 2000 may include one or more other peripheral output devices including, but not limited to, an audio speaker, a printer, and any combinations thereof. Such peripheral output devices may be connected to bus 2012 via a peripheral interface 2056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for utilizing diagnostics for informed vibrant constitutional guidance, the system comprising:
    at least a server;
    a diagnostic engine operating on the at least a server, wherein the diagnostic engine is configured to:
    train a machine learning model, wherein the machine-learning model is a trained machine-learning model trained by a first training data set and a second training data set;
    wherein the machine-learning model is configured to receive at least a biological extraction as an input and output a diagnostic output including at least a prognostic output and at least an ameliorative process output;
    wherein the first training data set includes a plurality of first data entries, each first data entry of the plurality of first data entries including at least an element of physiological state data and at least a correlated first prognostic label; and
    wherein the second training data includes a plurality of second data entries, each second data entry of the plurality of second data entries including at least a second prognostic label and at least a correlated ameliorative process label; and
    at least an advisory module, operating on the at least a server, the at least an advisory module designed and configured to:
        generate an advisory output as a function of the diagnostic output, wherein the advisory output comprises textual data identifying the diagnostic output and wherein the textual data identifying the diagnostic output is configured to be displayed on an advisor client device; and
        transmit the advisory output to the advisor client device.

2. The system of claim 1, wherein:
    the diagnostic engine further comprises a prognostic label learner; and
    the prognostic label learner is designed and configured to generate the at least a prognostic output as a function of the first training data set and at least a biological extraction.

3. The system of claim 2, wherein the prognostic label learner is designed and configured to generate the at least a prognostic output as a function of a classification of the at least a prognostic output.

4. The system of claim 3, wherein the classification of the prognostic label further comprises a progression of a medical condition.

5. The system of claim 1, wherein:
    the diagnostic engine further comprises an ameliorative label learner; and
    the ameliorative label learner is designed and configured to generate the at least an ameliorative output as a function of the second training data set and the at least a prognostic output.

6. The system of claim 5, wherein the ameliorative process label learner is designed and configured to generate the at least an ameliorative output as a function of a classification of the at least a prognostic output.

7. The system of claim 6, wherein the classification of the at least a prognostic output further comprises staging of at least a prognostic output.

8. The system of claim 1, wherein the advisory module is configured to receive at least an informed advisor input.

9. The system of claim 1, wherein the advisory output further comprises a textual entry field configured to be displayed on the advisor client device.

10. The system of claim 1, wherein the advisory output further comprises a relevance field.

11. A method of utilizing diagnostics for informed vibrant constitutional guidance the method comprising:
    training, by a diagnostic engine operating on the at least a server, a machine-learning model, wherein the machine-learning model is a trained machine-learning model trained by a first training data set and a second training data set;
    wherein the machine-learning model is configured to receive at least a biological extraction as an input and output a diagnostic output including at least a prognostic output and at least an ameliorative process output;
    wherein the first training data set includes a plurality of first data entries, each first data entry of the plurality of first data entries including at least an element of physiological state data and at least a correlated first prognostic label; and
    wherein the second training data includes a plurality of second data entries, each second data entry of the plurality of second data entries including at least a second prognostic label and at least a correlated ameliorative process label;
    generating, by an advisory module operating on at least the server, an advisory output as a function of the diagnostic output, wherein the advisory output comprises textual data identifying the diagnostic output and wherein the textual data identifying the diagnostic output is configured to be displayed on an advisor client device; and
    transmitting; by the advisory module operating on at least the server, the advisory output to the advisor client device.

12. The method of claim 11, wherein the prognostic label is generated by a prognostic label learner operating on the diagnostic engine, wherein the prognostic label learner is designed and configured to generate the at least a prognostic output as a function of the first training data set and at least a biological extraction.

13. The method of claim 12, wherein the prognostic output is generated as a function of a classification of the prognostic label.

14. The method of claim 11, wherein the ameliorative process label is generated by an ameliorative process label learner operating on the diagnostic engine, wherein the ameliorative process label learner designed and configured to generate the at least an ameliorative output as a function of the second training data set and the at least a prognostic output.

15. The method of claim 14, wherein the at least an ameliorative output is generated as a function of a classification of the at least a prognostic output.

16. The method of claim 11, wherein the advisory output further comprises a textual entry field.

17. The method of claim 11, further comprising generating, by a plan generation module operating on at least the server, a comprehensive instruction set associated with the user as a function of the diagnostic output and the at least an advisory output.

18. The method of claim 17, wherein generating the comprehensive instruction set further comprises:
   determining that a first prognostic label of the at least a prognostic output and a second prognostic label of the at least a prognostic output belong to a shared category; and
   adding a category label associated with the shared category to the comprehensive instruction set.

19. The method of claim 17, wherein generating the comprehensive instruction set further comprises:
   determining that a first ameliorative label of the at least an ameliorative output and a second ameliorative label of the at least an ameliorative output belong to a shared category; and
   adding a category label associated with the shared category to the comprehensive instruction set.

20. The method of claim 17 further comprising receiving at least an informed advisor input.

\* \* \* \* \*